(12) United States Patent
Taylor et al.

(10) Patent No.: US 11,478,348 B2
(45) Date of Patent: Oct. 25, 2022

(54) MEDICAL IMPLANTS HAVING MANAGED BIODEGRADATION

(71) Applicant: POLY-MED, INC., Anderson, SC (US)

(72) Inventors: Michael Scott Taylor, Anderson, SC (US); Jennifer Cartledge, Seneca, SC (US); Kenneth David Gray, Jr., Clemson, SC (US)

(73) Assignee: POLY-MED, INC., Anderson, SC (US)

( * ) Notice: Subject to any disclaimer, the term of this patent is extended or adjusted under 35 U.S.C. 154(b) by 142 days.

(21) Appl. No.: 16/310,786

(22) PCT Filed: Jun. 23, 2017

(86) PCT No.: PCT/US2017/039130
§ 371 (c)(1),
(2) Date: Dec. 17, 2018

(87) PCT Pub. No.: WO2017/223526
PCT Pub. Date: Dec. 28, 2017

(65) Prior Publication Data
US 2020/0121441 A1    Apr. 23, 2020

Related U.S. Application Data

(60) Provisional application No. 62/354,099, filed on Jun. 23, 2016.

(51) Int. Cl.
*A61F 2/04* (2013.01)

(52) U.S. Cl.
CPC .......... *A61F 2/04* (2013.01); *A61F 2002/048* (2013.01); *A61F 2210/0004* (2013.01); *A61F 2210/0076* (2013.01); *A61F 2240/001* (2013.01); *A61F 2250/0031* (2013.01)

(58) Field of Classification Search
CPC ................... A61F 2/04; A61F 2002/048; A61F 2210/0004; A61F 2210/0076; A61F 2240/001; A61F 2250/0031; A61F 2250/003; A61F 2/88; A61F 2/90; A61F 2/82; A61L 31/10; A61L 31/148; A61L 31/16; A61L 31/14; A61M 27/008
See application file for complete search history.

(56) References Cited

U.S. PATENT DOCUMENTS

| 7,179,283 | B2 | 2/2007 | Dimatteo et al. |
| 8,182,890 | B2 | 5/2012 | Zheng et al. |
| 9,078,957 | B2 | 7/2015 | Sabaria |
| 2003/0153971 | A1 | 8/2003 | Chandrasekaran |
| 2003/0153972 | A1* | 8/2003 | Helmus .................. A61L 31/10 623/1.15 |

(Continued)

FOREIGN PATENT DOCUMENTS

WO    2015112915    7/2015

OTHER PUBLICATIONS

International Search Report and Written Opinion dated Oct. 30, 2017, for International Application No. PCT/US2017/039130.

*Primary Examiner* — Jennifer Dieterle
*Assistant Examiner* — Rebecca Lynee Zimmerman

(57) ABSTRACT

Medical implants that include a containment layer surrounding, or surrounded by, a biodegradable medical device provide the benefit that pieces formed during degradation of the medical device are held within a constrained place and thus do not causes injury to a hosts.

10 Claims, 3 Drawing Sheets

(56) References Cited

U.S. PATENT DOCUMENTS

| | | | |
|---|---|---|---|
| 2003/0199993 A1* | 10/2003 | Gellman | A61L 27/44 623/23.75 |
| 2006/0178739 A1* | 8/2006 | Shalaby | A61L 31/128 623/1.49 |
| 2006/0229711 A1* | 10/2006 | Yan | A61F 2/02 623/1.38 |
| 2007/0224244 A1* | 9/2007 | Weber | A61L 27/34 424/426 |
| 2007/0282432 A1* | 12/2007 | Stinson | A61L 31/148 623/1.38 |
| 2008/0069858 A1 | 3/2008 | Weber | |
| 2009/0208555 A1* | 8/2009 | Kuttler | A61F 2/82 424/426 |
| 2014/0172118 A1 | 6/2014 | Pendleton et al. | |
| 2015/0164663 A1 | 6/2015 | Shalaby et al. | |
| 2015/0335794 A1 | 11/2015 | Piveteau et al. | |

* cited by examiner

MEDICAL IMPLANTS HAVING MANAGED BIODEGRADATION

CROSS-REFERENCE TO RELATED APPLICATION

This application is a national phase application under 35 U.S.C. § 371 of International Application No. PCT/US2017/039130, filed Jun. 23, 2017, which claims the benefit under 35 U.S.C. § 119(e) of U.S. Provisional Patent Application No. 62/354,099 filed Jun. 23, 2016, which applications are incorporated herein by reference in their entireties for all purposes.

FIELD OF THE INVENTION

The present invention relates generally to biodegradable medical implants and uses thereof.

BACKGROUND

Some medical implants are only necessarily present in a host for a limited period of time. After the period of time has passed, the implant may be physically removed, although that often requires additional medical intervention. Alternatively, the implant may be left in place indefinitely. This option is satisfactory in those cases where the long-term presence of the implant is not harmful and when a permanent implant is necessary for the particular treatment. As another alternative, the implant may be formed from a bioabsorbable material. A bioabsorbable material will degrade and/or absorb within the host and the components and metabolites thereof will eventually be excreted. Bioabsorable implants are increasingly desired by health care providers, however those implants sometimes cause undesired results, e.g., the host does not tolerate the degradation products.

There is a need in the art for medical implants that do not cause harm to the host as they degrade, or at the very least cause reduced harm to the host as they degrade. The present invention is directed to fulfilling that need.

SUMMARY

The present disclosure is directed, in one aspect, to medical implants that degrade within a host, where that degradation is managed to occur in a particularly desirable manner due to physical or chemical features that are incorporated into the implant. For example, the implant may include a containment layer that surrounds all or part of the implant, where that containment layer is constructed in such a way that the implant degrades in a different manner than it would degrade absent the implant. As another example, the implant may purposely include defects that are particularly vulnerable to degradation, where these defects provide sites where degradation will preferentially occur vis-à-vis other sites of the implant. In one embodiment, the defect does not provide any functional benefit to the device, e.g., the defect does not make the device stronger or work any better, but is present solely to impact the degradation profile of the implant. As yet another example, the implant may contain a compositional vector, which means that the composition of the implant will vary along a dimension, e.g., along the length of the implant. The varying composition will have a corresponding varying susceptibility to degradation under the conditions to which the implant are exposed within the host. By this approach, for instance, one end of the implant can be caused to degrade before the other end degrades. As a final example, the implant may include a compositional inhomogeneity where the site(s) of the inhomogeneity are either more or less susceptible to degradation than are the neighboring homogeneous sites of the implant. For instance, the implant may include particles dispersed in a polymer, where the polymer is homogeneous and the particles provides an inhomogeneity that is more susceptible to degradation than is the polymer, or acts as an initiation site for degradation of the polymer. These are examples of managed degradation according to the present disclosure, whereby medical implants that degrade within a host are constructed in such a way that degradation is managed to occur in a particularly desirable manner due to physical or chemical features that are incorporated into the implant by the construction of the implant.

In one exemplary embodiment, the present invention is directed to a medical implant comprising a containment layer that at least partially encases a medical device, the medical device being at least partially degradable when the implant is implanted in a host, the containment layer being either nonbiodegradable or biodegradable, however when the containment layer is biodegradable, it degrades more slowly than the portion of the medical device which it is surrounding.

Optionally, the containment layer serves as a container for pieces of the medical device that form during the degradation of the medical device. Optionally, the device provides structural support within a host, where also optionally that device is a stent, such as an endoureteral stent. The containment layer may be a coating on the medical device, where the coating is optionally hydrophilic. When the coating is biodegradable, it should have a slower rate of degradation than the medical device which is encased by the coating.

In another exemplary embodiment, the present disclosure provides a medical implant comprising a containment layer that is at least partially encased by a medical device, where the containment layer at least partially encases a hollow center of the medical device, the medical device being at least partially biodegradable when the implant is implanted in a host, the containment layer being either nonbiodegradable or biodegradable, where the containment layer provides a barrier between the degradation product(s) of the medical device that form during the degradation of the medical device and the hollow center of the medical device. Alternatively, the containment layer may fully encase the medical device by covering the internal and external structures of a stent, for example, a ureter stent.

The containment layer manages the degradation of the device, which may also include the movement of the device, e.g., excretion of the device. In one option, the containment layer may be a coating that is located on or within the medical device. In another option, the containment layer may be a mesh that is located on or within the medical device. The containment layer may cover only a portion of the medical device, e.g., the end of a tubular medical device may have a cap that serves as a containment layer.

The present disclosure describes a number of medical devices, where any of the described medical devices may be modified to exhibit managed degradation by means disclosed herein. For example, any of the medical devices may be modified to include a slit, or to have polymeric components that are selectively degraded to have a gradient of molecular weight, to thereby provide a degradation profile for the device which is managed to occur in a particularly desirable manner due to the physical or chemical features that are incorporated into the implant according to the present disclosure.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, and the claims.

BRIEF DESCRIPTION OF THE DRAWINGS

In FIG. 2, a portion of the knit (12) has been omitted so that it is possible to see the coil (10) that lies underneath the knit (12).

FIG. 3 also shows a coil (10) and a knit (12).

FIG. 4 also shows a coil (10) and a knit (12).

DETAILED DESCRIPTION

Figure 1:
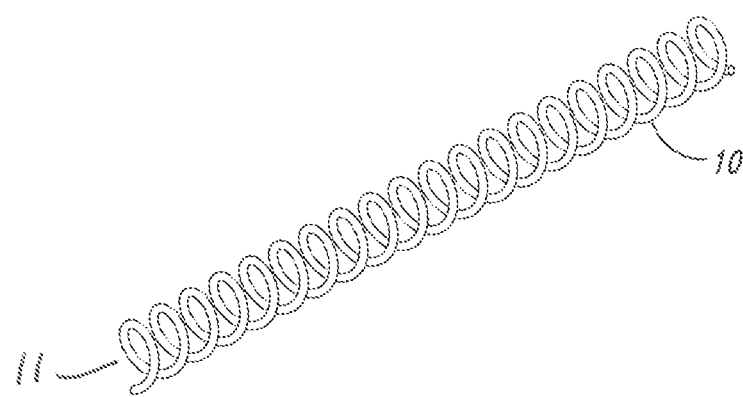
FIG. 1 is a perspective view of a coil (10) having a hollow center (11).
Figure 2:
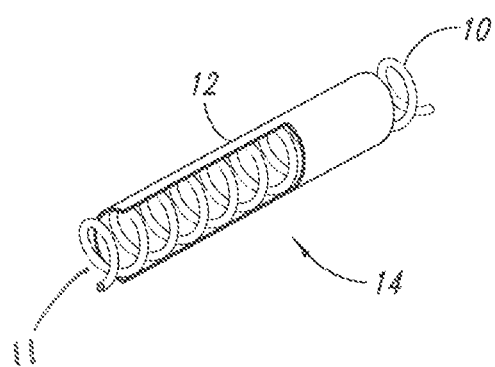
FIG. 2 is a perspective view of the coil (10) having a hollow center of FIG. 1 with a knit (12) that adjoins the coil (10) to provide a knitted core that may also be referred to as a medical device (14). The medical device (14) may be a stent, such as an endoureteral stent.
Figure 3:
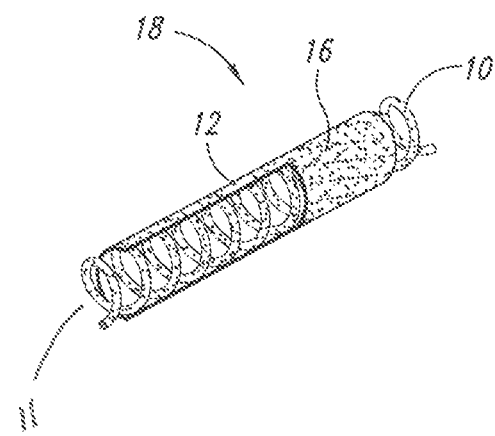
FIG. 3 is a perspective view of the medical device (14) of FIG. 2 to which a coating (16) has been applied, where the coating (16) is illustrated by the speckling in FIG. 3 that is not present in FIG. 2. The addition of the coating (16) to the medical device (14) results in a medical implant (18) of the present disclosure. The coating (16) functions as a containment layer, where the containment layer at least partially encases a hollow center (11) of the medical device.
Figure 4:
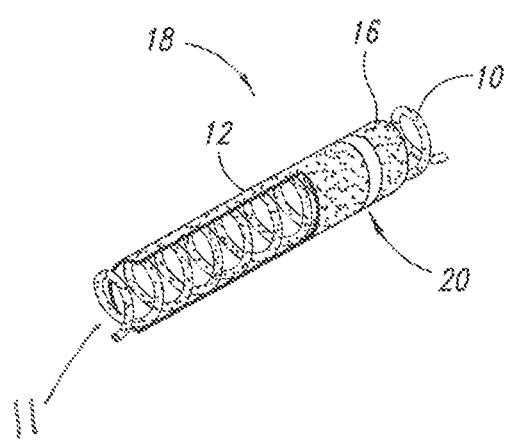
FIG. 4 is a perspective view of the medical device (14) of FIG. 2 to which a coating (16) with a defect (20) has been partially applied, where the coating (16) is illustrated by the speckling in FIG. 3 that is not present in FIG. 2. The coating (16) is illustrated by the speckling in FIG. 4 that is not present in FIG. 2. The addition of the coating (16) to the medical device (14) results in a medical implant (18) with a defect (20) of the present disclosure. The coating (16) functions as a containment layer, where the containment layer at least partially encases a hollow center (11) of the medical device.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art. The headings used within this document are only being utilized to expedite its review by the reader, and should not be construed as limiting the invention or claims in any manner.

As used throughout this document, including the claims, the singular form "a", "an", and "the" include plural references unless indicated otherwise. For example, "a" polymer includes one or more polymer. As another example, "a" layer refers to one or more layers.

"Degrade" as in a degradable medical device means that the medical device, when implanted into a host at a location in the host that is intended for the device, will break down or deteriorate in either a chemical or structural sense. For example, a device that breaks into pieces, e.g., it breaks in half or it disintegrates into many piece, is a device that has degraded in a structural sense. When the device softens while implanted, then that device degrades in a structural sense. When some or all of a device dissolves into the biological fluid with which the device is in contact, then that device chemically degrades. Chemical degradation also includes the occurrence of degradation reactions such as hydrolysis, oxidation, and enzymatic bond cleavage. An absorbable or bioadsorbable medical device is a device that will degrade in the host. A degradable implantable medical device refers to an implantable medical device that is intended by the manufacturer and/or the health care provider who recommends the device to have a desirably limited lifetime in the host. In other words, the manufacturer and/or health care provider have made and/or selected the device, in part, because it should naturally degrade in the host and not become a permanent fixture within the host.

"Degradation profile" refers to a description of how the implant degrades. The degradation profile may provide a time course for the implant degradation as well as a geometric description of the degradation during the time course. For example, the implant may have a degradation profile whereby the implant degrades along its length from top to bottom over the course of a specified number of days.

"Host" refers to mammals, e.g., humans, dogs, cats, and livestock. The host may also be referred to as a patient or as a subject.

An implantable "medical device" as used herein refers to a device such as an instrument or apparatus, intended to be implanted into the body of a host by a heath care provider. The medical device provides medical (as opposed to, e.g., purely cosmetic) purposes or benefits, in that it improves the health of the host through any one or more of diagnosing, preventing, treating or curing an undesirable medical condition such as a disease. The medical device may be an accessory device which does one or more of: supports the performance of a parent medical device by enabling or facilitating that parent device to perform according to its intended use; supplements the performance of a parent device by adding a new function or a new way of using the parent device, without changing the intended use of the parent device; or augments the performance of a parent device by enabling the device to perform its intended use more safely or effectively. The medical device does not achieve its purpose solely through chemical action within the body, and the medical device does not achieve its purpose upon being metabolized.

In one aspect, the medical device is used in maintaining or creating patency of a conduit, e.g., a tube or vessel, within a host. Exemplary tubes and vessels are found, for example, along the gastrointestinal (GI) tract of a host, e.g., in the esophagus, the intestine including the transverse colon, the descending colon, the ascending colon, the sigmoid colon and the small intestine, where the small intestine includes the duodenum, the jejunum, and the ileum, the cecum, and the rectum. In one embodiment the medical implant is designed to be implanted in the ureter, i.e., the tube that carries urine from the kidney to the urinary bladder. In another embodiment, the medical implant is designed to be implanted in the urethra, i.e., the tube that transports urine from the urinary bladder to outside the host. Other exemplary tubes and vessels are found in organs such as the heart, pancreas, prostate gland, and the kidney. Another location a tube or vessels exists in a host and which may be implanted with a medical implant according to the present disclosure is the breast ducts which transport milk from the lobules (milk-producing glands) to the nipple. Other locations for a medical implant include the ear and the sinuses.

In one aspect, the medical device is formed, at least in part, from one or more of a thermoplastic or thermoset or elastomeric polymer. In one aspect, the medical device is sterile. In one aspect, the medical device is intended to be wholly implanted into the host, i.e., to entirely lie under the skin of the host, as opposed to, e.g., a hearing aid that sits in the ear, a dental prosthetic which sits in the mouth of the host, or a contact lens which sits on the eye of a host. In one aspect, the implantable medical device is intended to be implanted in a body passageway such as a tube or vessel. Examples of implantable medical devices, which may also be degradable, include stents, shunts, sutures and surgical meshes. Implantable medical devices are also described in the following patent documents: U.S. Pat. Nos. 8,753,387; 8,101,104; 7,594,928; and US 2014/0288636.

"Medical implant" refers to a device of the present invention that includes both a degradable implantable medical device and a containment layer located adjacent to at least a portion of the medical device.

Briefly stated, the present invention provides medical implants that include a bioabsorbable medical device and a containment layer therefor. During the process of bioabsorption within a host, the medical device degrades. In order to manage this degradation process, e.g. to manage the timing of the degradation, the type of degradation, the extent of degradation, and the movement of the degraded medical device including portions thereof within the host, the medical implant includes one or more containment layers. The containment layer may, for example, stop the degradation pieces from dispersing within the host and possibly damaging neighboring tissue and/or organs. In one aspect, the containment layer at least partially, and optionally fully, encases the medical device. When the medical device degrades into pieces, the containment layer will encase the disintegrating medical device and will maintain sufficient structural integrity to hold, or at least assist in holding, the pieces together within a confined space. The containment layer is able to influence and direct the elimination of the medical device from the host, including any pieces that form therefrom.

In one aspect, the present disclosure provides a degradable medical device. The following describes degradable compositions that may be used to form medical devices and/or components thereof, as well as containment layers that may be a part of, or added onto, a medical device.

In general, medical devices and containment layers may be made from biostable or non-biostable materials, where non-biostable materials are referred to herein as degradable materials, and may be known in the art as any of biodegradable, absorbable or bioabsorbable, erodible or bioerodable, soluble or biosoluble. Degradable polymers are capable of being completely eroded or absorbed when exposed to bodily fluids such as blood and can be gradually resorbed, absorbed and/or eliminated by the body. Some degradable materials absorb due to chemical degradation that occurs to the material upon exposure to bodily fluid such as may be found in the vascular environment of a host. Chemical degradation refers to degradation of a material due to chemical reaction of the material with bodily fluids or substances within bodily fluids. The chemical degradation can be the result of hydrolysis, oxidation, enzymolysis, and/or metabolic processes, etc. The chemical degradation can result in, for example, a decrease in molecular weight, deterioration of mechanical properties, and decrease in mass due to erosion. Mechanical properties may correspond to strength and modulus of the material. Deterioration of the mechanical properties of the material decreases the ability of a medical device made therefrom to function optimally in the host. For example, if the device is a stent, the stent provides diminishing mechanical support in a vessel as it degrades. Additionally, some degradable materials are water soluble. A water soluble material refers to a material that is capable of dissolving in water in addition to, or even in the absence of chemical degradation of the material.

In one embodiment, the degradable medical device or containment layer is formed, in whole or in part from a degradable organic polymer. The organic polymer may be, for example, thermoplastic or thermoset or elastomeric polymer. The organic polymer may be a copolymer, where copolymer are made from two or more different monomers so as to provide properties that are not readily available from a homopolymer. The organic polymer may be in admixture with one or more different polymers, such as one or more different organic polymers. Thus, the various degradable organic monomers as identified herein may be used in concert to prepare a homopolymer or a copolymer, and the various organic polymers as identified herein may be used in combination to prepare an admixture. The medical devices of the present disclosure are degradable, and accordingly will contain some degradable components. In one embodiment, the medical device is made entirely from degradable materials, and thus the medical device is completely degradable. In another embodiment, the medical device is mostly made from degradable materials, and thus at least 50 wt % of the medical device is degradable. In another embodiment, the medical device is made from both degradable and biostable materials, and thus less than 100% of the medical device will degrade. In various embodiments, 100% or up to 95%, or up to 90%, or up to 85%, or up to 80%, or up to 75%, or up to 70%, or up to 65%, or up to 60%, or up to 55%, or up to 50%, or up to 45%, or up to 40%, or up to 35%, or up to 30%, or up to 25% of the medical device is made from degradable material(s), these percentage values being wt % based on the weight of the implantable medical device.

Examples of degradable polymers which may be used to prepare a containment layer or medical device of the present disclosure include poly(alpha-hydroxy acid) polymers and copolymers, such as polymers and copolymers of glycolide including polyglycolide (PGA), poly(glycolide-co-lactide) (PGLA), and poly (glycolide-co-trimethylene carbonate (PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly(lactide-co-trimethylene carbonate), poly(lactide-co-delta-valerolactone), poly(lactide-co-epsilon-caprolactone), poly(glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-betahydroxyvalerate); polygluconate; poly(beta-hydroxypropionate) (PHPA); poly(beta-dioxanone)(PDS); poly(delta-valerolactone); poly(ε-caprolactone); methylmethacrylate-N-vinylpyrrolidone copolymers; polyester amides; polyesters of oxalic acid; polydihydropyranes; poly(alkyl-2-cyanoacrylate); polyvinyl alcohol (PVA); polypeptides; poly(beta-maleic acid)(PMLA); poly(beta-alkanoic acid); poly(ethylene oxide) (PEO); polyanhydrides, polyphosphoester, and chitin polymers.

In one embodiment the organic polymer is a polyester. For example, the polymer may be a polyester selected from poly(α-hydroxy acid) homopolymers, poly(alpha-hydroxy acid) copolymers and blends thereof. In addition or alternatively, the polyester may be selected from polyglycolide, poly-L-lactide, poly-D-lactide, poly-DL-lactide, and blends thereof. The polyester may be selected from polymers and copolymers of polylactide (PLA), including poly-L-lactide (PLLA), poly-D-lactide (PDLA), poly-DL-lactide (PDLLA).

In one embodiment, the organic polymer is semicrystalline, or is capable of being formed into fibers, or is both semicrystalline and fiber forming. In one embodiment, a containment layer is prepared using an organic polymer that is at least one of semicrystalline and fiber-forming. In one embodiment, a degradable stent is prepared with an organic polymer that is both semicrystalline and fiber forming. To additionally make the organic polymer fast-degrading, glycolide may be used as the, or one of the, monomer(s) used to form the organic polymer. Para-dioxane (PDO) is another suitable monomer for forming fast-degrading organic polymers, where the corresponding homopolymer is known as poly(PDO). Poly(PDO) typically degrades more slowly that glycolide-based polymer, so in order to prepare a very fast degrading organic polymer, the monomer feed is preferably rich in glycolide.

In one embodiment, the organic polymer has a polyaxial structure, while in another embodiment the organic polymer is linear. The polyaxial structure may be a part of the organic polymer, for example, it may be present in a block of a block copolymer. Another option is for the organic polymer to be a segmented polyaxial that is semicrystalline and fiber-forming, and glycolide-based to ensure fast degradation. Yet another option is to use linear copolymers for either or both of: diblock, triblock, pentablock, wherein the central block is amorphous and the other blocks are semicrystalline, except for the pentablock, which may be PEG as the central block with amorphous segments connected to the outer crystalline segments (forming a symmetrical pentablock polymer that is a polyether-ester; all other polymers being referred to are aliphatic polyesters). The linear block copolymers may also be comprised of semicrystalline blocks in all cases, with no amorphous blocks, resulting in polymers that can be oriented after fiber formation to create alternating patterns of different crystalline structure and percentage in the fiber, such that there is slight differences in degradation profile of the alternating blocks forming the fiber (as a fiber is oriented, horizontal strips of crystalline regions form and align the blocks comprising the polymer chain). Alternatively, unblocked linear copolymers can be substituted. In one embodiment, these organic polymers are used to form fibers, and the fibers are used to form the containment layer. In another embodiment, these organic polymers are not formed into fibers, however the organic polymer is used to form a containment layer, e.g., by simply spraying a solution of the polymer onto the medical device, or by dip coating, etc.

The containment layer or medical device may be made from a base polymer that is amorphous, compliant and elastomeric. It can also be crystallizable, but too much crystallinity typically reduces the compliant nature of the polymer. If a higher crystalline material is chosen for use, then it may be advisable to incorporate a plasticizer such as PEG into the layer in order to reduce the final crystallinity of the layer when applied to the medical device. As mentioned above, the polymer can be polyaxial or linear, blocked or segmented or random. For a flexible and compliant containment layer, the organic polymer(s) may be minimally crystallinity or may be amorphous.

The organic polymer may be prepared from a prepolymer and end-graft(s) if it is a block copolymer, or it may not be prepared from a prepolymer. In one embodiment, one or more monomers selected from caprolactone, trimethylene carbonate, and/or l-lactide are used to form the organic polymer for the containment layer in order to extend the degradation time frame beyond that of the medical device.

Suitable degradable organic polymers other than polyesters include polyether-esters, polyether-ester-urethanes (bioabsorbable urethanes), polyether-urethanes and polyether-urethane-ureas, the latter examples being very slowly and typically incompletely degradable.

In various embodiment, the medical device and/or containment layer is made from any of the following polymers. MG-5 (Poly-Med, Anderson, S.C.), which has >65% glycolide in end-graft, is a semicrystalline, polyaxial block copolyester, prepared in a two-step reaction from an amorphous prepolymer and crystalline end graft. MG-9 (Poly-Med, Anderson, S.C.), which has >80% glycolide, is a semicrystalline, polyaxial block copolyester, prepared in a two-step reaction from an amorphous prepolymer and crystalline end graft. A semicrystalline, polyaxial segmented copolyester prepared in a single step reaction (no prepolymer is used). A semicrystalline, linear block copolyester, prepared in a two-step reaction from an amorphous prepolymer and crystalline end graft. A triblock copolymer with crystalline end grafts. A diblock copolymer. A semicrystalline, linear segmented copolyester prepared in a single step reaction (i.e., no prepolymer is used). SVG-12 (Poly-Med, Anderson, S.C.) having an inherent viscosity of greater than 1.0, having a crystallizable end graft. A polyaxial block copolymer. A polymer prepared from an amorphous prepolymer and amorphous end graft. A linear block copolymer (triblock, diblock, pentablock). A linear, segmented copolymer. A linear random copolymer which is amorphous and thus is both compliant and flexible. The foregoing are exemplary only of the organic polymers that may be used to prepare a suitable medical device, component thereof, or containment layer.

Another suitable polymer is a mixture comprising (a) a bioerodible polyester network formed by reaction between reactive species that comprise a polyol and a polycarboxylate, wherein at least one of the polyol and polycarboxylate has a functionality of three or more, and (b) a bioerodible thermoplastic polymer. Optionally, one or more of the following may further characterize this compositions: the polyol is selected from a non-polymeric diol, a polymeric diol, a non-polymeric triol, a polymeric triol; the polycarboxylate is selected from a non-polymeric dicarboxylate, a polymeric dicarboxylate, a non-polymeric tricarboxylate, and a polymeric tricarboxylate; the reactive species comprise a triol, a tricarboxylate, or both; the reactive species comprise (a) non-polymeric tricarboxylate and (b) a polyester polyol; the reactive species comprise (a) citric acid and (b) a polycaprolactone diol, a polycaprolactone triol or both;

the bioerodible thermoplastic polymer has a melting point above body temperature; the bioerodible thermoplastic polymer has a glass transition temperature below room temperature; and the bioerodible thermoplastic polymer is a bioerodible thermoplastic polyester. See, e.g., U.S. Patent Publication No. 20160166739.

In one aspect, the medical implants of the present disclosure include a containment layer in addition to a medical device. The location of the containment layer relative to the medical device, and the properties of the containment layer in terms of physical and chemical properties, both assist in managing the degradation and/or elimination of the medical implant from the host. In particular, the containment layer serves, in part, to manage the degradation and/or elimination of the medical device from the host. The properties of the containment layer should also be selected with a view to managing the degradation and/or elimination of the containment layer itself from the host.

The medical devices present in the medical implants of the present disclosure are degradable to at least some extent. In other words, the medical device will degrade when placed into the host. That degradation may be a physical or chemical degradation. Physical degradation refers to a change in the physical or mechanical properties of the medical device. For example, the device may break down into pieces, and thus lose its integrity. As another example, the device may soften and become compliant. As yet another example, the device may absorb fluid and swell. In each of these cases, the device undergoes a change in physical or mechanical properties. Chemical degradation refers to a change in chemical composition. For example, an organic polymer from which the device is made may undergo hydrolytic bond cleavage or enzymatically-induced bond cleavage, and thereby lose molecular weight. As another example, water-soluble components of the medical device may dissolve in water and leave the vicinity of the medical device. In each of these example, the chemical degradation produces a change in the chemical description of the medical device. It may be the case that degradation of the medical implant simultaneously achieves physical as well as chemical degradation. In any event, the containment layer of the present disclosure may serve, in part or entirely, to influence this degradation. Thus, the properties of containment layer can be used to manage the degradation and/or elimination of the medical implant from the host.

In one aspect, the containment layer provides a physical barrier between the tissue of a host and the medical device. Such a barrier is useful, for example, when the device degrades by breaking into pieces and it is desired to manage the dispersement or dissemination of those pieces. For example, in one embodiment the containment layer may be relatively long-lasting compared to the medical device, so that as the medical devices is breaking into pieces, the containment layer is maintaining sufficient structural integrity that those pieces are retained within the containment layer. Such a containment layer is useful when the medical device is implanted in the kidney and it is undesirable that pieces from the medical device should contact the inside of the kidney and calcify. In a related embodiment, the containment layer is again relatively long lasting compared to the medical device which is an esophageal stent. In this case, if the esophageal stent breaks into pieces, the containment layer which is located in and surrounds the lumen wall of the stent, will deter those pieces from passing into the stomach. Thus, in either example the containment layer effectively restricts the movement pieces of the medical device.

In another aspect, the containment layer provides a physical or chemical barrier between the degradation-inducing fluids of the host and the medical device. This layer can be used to influence the spatial and temporal degradation of the medical device. For example, in one embodiment the containment layer is a discontinuous layer such that the layer covers some but not all of the medical device. In this situation, the containment layer effectively acts as a barrier between the medical device and the degradation-causing fluid of the host, which restricts contact between the medical device and the fluid. The containment layer thereby allows the exposed portion(s) of the medical device to degrade more quickly than will the nonexposed portion(s) of the medical device. In this way, the containment layer is used to manage where the device will initially degrade.

In another embodiment, a graduated containment layer is used to manage the spatial and temporal degradation and/or elimination of the medical device. For example, a medical device may have a single coating layer over a first portion of the device, a double coating layer over a second portion of the device, and a triple coating layer over a third portion of the device. Assuming the composition of the coating layer is the same at each location, the first portion of the medical device will begin to degrade before the second and third portions of the device. Depending on the relative thicknesses at each location, the first portion may significantly degrade and be eliminated from the host, while the second and third portions of the device are still significantly intact. The degradation and elimination of the first portion of the medical device will allow increased access of biological fluid to the second portion of the medical device, with the result that the second portion will undergo degradation even though the second portion may still be covered by the containment layer. The second portion of the device will undergo degradation and elimination, followed by degradation and elimination of the third portion of the device. In this example, the containment layer manages the rate at which various portions of a medical device degrade and are eliminated from the host. However, it should be noted that the containment layer may also function to manage the dispersement or dissemination of those pieces, i.e., to restrict the movement of those pieces within the host.

The medical implant, including one or both of the medical device itself and the containment layer thereof, may include a therapeutic agent. The amount of the therapeutic agent incorporated into the implant will depend on the nature of the implant, the actual therapeutic agent, the condition of the subject, and so forth. The amount may be readily determined by those of ordinary skill in the art. Exemplary therapeutic agents include anti-thrombotic agents, anti-proliferative agents, anti-inflammatory agents, anti-migratory agents, antineoplastic agents, anti-mitotic agents, anesthetic agents, and anti-coagulants. Addition suitable therapeutic agents include agents that affect extracellular matrix production and organization, vascular cell growth (either promoters or inhibitors), cholesterol-lowering agents, vasodilating agents, and agents that interfere with endogenous vasoactive mechanisms.

In various embodiments of the present invention, the medical device may be an ureteral stent. The medical device, e.g., the ureteral stent, may be designed to release one or more drugs where representative examples of drugs include one or more suitable members of the following: alpha-adrenergic blockers, analgesic agents, anti-cancer agents, antineoplastic agents, anti-inflammatory agents, anti-microbial agents, antiproliferative agents, anti-spasmodic agents, beta-adrenergic agonists, bronchodilators (e.g., for muscle relaxant properties), calcium channel blockers, corticosteroids, anesthetic agents, narcotic analgesic agents, nitric oxide donors, nitric oxide releasing compounds, non-narcotic analgesic agents, prostaglandins, and among others, as well as combinations thereof.

Additional representative examples of drugs include one or more of the following: Angiogenesis Inhibitors, 5-Lipoxygenase Inhibitors and Antagonists, Chemokine Receptor Antagonists CCR (1, 3, and 5), Cell Cycle Inhibitors, Cyclin Dependent Protein Kinase Inhibitors, EGF (Epidermal Growth Factor) Receptor Kinase Inhibitors, Elastase Inhibitors, Factor Xa Inhibitors, Farnesyltransferase Inhibitors, Fibrinogen Antagonists, Guanylate Cyclase Stimulants, Heat Shock Protein 90 Antagonists, HMGCoA Reductase Inhibitors, Hydroorotate Dehydrogenase Inhibitors, IKK2 Inhibitors, IL-1, ICE and IRAK Antagonists, IL-4 Agonists, Immunomodulatory Agents, Inosine monophosphate dehydrogenase inhibitors, Leukotriene Inhibitors, MCP-1 Antagonists, MMP Inhibitors, NF kappa B Inhibitorsm NO Agonists, P38 MAP Kinase Inhibitors, Phosphodiesterase Inhibitors, TGF beta Inhibitors, TNFa Antagonists and TACE Inhibitors, Tyrosine Kinase Inhibitors, Vitronectin Inhibitors, Fibroblast Growth Factor Inhibitors, Protein Kinase Inhibitors, PDGF Receptor Kinase Inhibitors, Endothelial Growth Factor Receptor Kinase Inhibitors, Retinoic Acid Receptor Antagonists, Platelet Derived Growth Factor Receptor Kinase Inhibitors, Fibronogin Antagonists, Antimycotic Agents, Bisphosphonates, Phospholipase A1 Inhibitors, Histamine H1/H2/H3 Receptor Antagonists, Macrolide Antibiotics, GPIIb IIIa Receptor Antagonists, Endothelin Receptor Antagonists, Peroxisome Proliferator-Activated Receptor Agonists, Estrogen Receptor Agents, Somatostatin Analogues, Neurokinin 1 Antagonists, Neurokinin 3 Antagonist, Neurokinin Antagonist, VLA-4 Antagonist, Osteoclast Inhibitor, DNA topoisomerase ATP Hydrolysing Inhibitor, Angiotensin I Converting Enzyme Inhibitor, Angiotensin II Antagonist, Enkephalinase Inhibitor, Peroxisome Proliferator-Activated Receptor Gamma Agonist Insulin Sensitizer, Protein Kinase C Inhibitor, CXCR3 Inhibitors, Itk Inhibitors, Cytosolic phospholipase A2-alpha Inhibitors, PPAR Agonist, Immunosuppressants, Erb Inhibitor, Apoptosis Agonist, Lipocortin Agonist, VCAM-1 antagonist, Collagen Antagonist, Alpha 2 Integrin Antagonist, TNF Alpha Inhibitor, Nitric Oxide Inhibitor, and Cathepsin Inhibitor.

Examples of alpha-adrenergic blockers include: alfuzosin, amosulalol, arotinilol, dapiprazole, doxazosin, ergoloid, fenspiride, idazoxan, indoramin, labetalol, manotepil, mesylates, naftopidil, nicergoline, prazosin, tamsulosin, terazosin, tolazoline, trimazosin, and yohimbine.

Examples of anesthetic agents include: benzocaine, cocaine, lidocaine, mepivacaine, and novacaine.

Examples of beta-adrenergic agonists include: albuterol, bambuterol, bitolterol, carbuterol, clenbuterol, clorprenaline, denopamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, prenalterol, procaterol, protokylol, reproterol, rimiterol, ritodrine, salmerterol, soterenol, terbutaline, tretoquinol, tulobuterol and xamoterol.

Examples of anti-cancer, anti-proliferative and antineoplastic agents include: agents affecting microtubule dynamics (e.g., colchicine, Epo D, epothilone, paclitaxel, vinblastine, vincristine, etc.), alkyl sulfonates, angiogenesis inhibitors (e.g., angiostatin, endostatin, squalamine, etc.), antimetabolites such as purine analogs (e.g., 6-mercaptopurine or cladribine, which is a chlorinated purine nucleoside analog, etc.), pyrimidine analogs (e.g., 5-fluorouracil, cytarabine, etc.) and antibiotics (e.g., daunorubicin, doxorubicin, etc.), caspase activators, cerivastatin, cisplatin, ethylenimines, flavopiridol, limus family drugs (e.g., everolimus, sirolimus, tacrolimus, zotarolimus, etc.), methotrexate, nitrogen mustards, nitrosoureas, proteasome inhibitors, and suramin.

Examples of antimicrobial agents include: benzalkonium chlorides, chlorhexidine, nitrofurazone, silver particles, silver salts, metallic silver and antibiotics, such as gentamicin, minocycline and rifampin, triclosan.

Examples of bronchodilators include: (a) ephedrine derivatives such as albuterol, bambuterol, bitolterol, carbuterol, clenbuterol, clorprenaline, dioxethedrine, ephedrine, epinephrine, eprozinol, etafedrine, ethylnorepinephrine, fenoterol, formoterol, hexoprenaline, isoetharine, isoproterenol, mabuterol, metaproterenol, n-methylephedrine, pirbuterol, procaterol, protokylol, reproterol, rimiterol, salmeterol, soterenol, terbutaline and tulobuterol, (b) quaternary ammonium compounds such as bevonium methyl sulfate, flutropium bromide, ipratropium bromide, oxitropium bromide and tiotropium bromide, (c) xanthine derivatives such as acefylline, acefylline piperazine, ambuphylline, aminophylline, bamifylline, choline theophyllinate, doxofylline, dyphylline, etamiphyllin, etofylline, guaithylline, proxyphylline, theobromine, I-theobromineacetic acid and theophylline, and (d) other bronchodilators such as fenspiride, medibazine, methoxyphenanime and tretoquinol, among others, as well as combinations and pharmaceutically acceptable salts, esters and other derivatives of the forgoing.

Examples of calcium channel blockers include: arylalkylamines (including phenylalkylamines) such as bepridil, clentiazen, fendiline, gallopamil, mibefradil, prenylamine, semotiadil, terodiline and verapamil, benzothiazepines such as diltiazem; calcium channel blockers such as bencyclane, etafenone, fantofarone, monatepil and perhexiline, among other calcium channel blockers; dihydropyridine derivatives (including 1,4-dihydropyridine derivatives) such as amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine and nitrendipine, piperazine derivatives such as cinnarizine, dotarizine, flunarizine, lidoflazine and lomerizine.

Examples of corticosteroids include: betamethasone, cortisone, deflazacort, dexamethasone, hydrocortisone, methylprednisolone, prednisolone, prednisone and triamcinolone, among others, as well as combinations and pharmaceutically acceptable salts, esters and other derivatives of the same.

Examples of nitric oxide donors/releasing molecules include: inorganic nitrates/nitrites such as amyl nitrite, isosorbide dinitrate and nitroglycerin, inorganic nitroso compounds such as sodium nitroprusside, sydnonimines such as linsidomine and molsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of, natural polymers/oligomers, oligosaccharides, peptides, polysaccharides, proteins, and synthetic polymers/oligomers), as well as C-nitroso-compounds, L-arginine, N-nitroso-compounds, and O-nitroso-compounds.

Examples of prostaglandins and analogs thereof for use in the present disclosure may be selected from suitable members of the following: prostaglandins such as PGE1 and PGI2 and prostacyclin analogs such as beraprost, carbacyclin, ciprostene, epoprostenol, and iloprost.

Examples of narcotic analgesic agents include: codeine, fentanyl, hydromorphonein, levorphanol, meperidine, methadone, morphine, oxycodone, oxymorphone, propoxyphene, and pentazocine, among others, as well as combinations and pharmaceutically acceptable salts, esters and other derivatives of the same.

Examples of non-narcotic analgesic agents include: analgesic agents such as acetaminophen, and non-steroidal anti-inflammatory drugs such as aspirin, celecoxib, diflunisal, diclofenac, etodolac, fenoprofen, flurbiprofen, ibuprofen, ketoprofen, ketorolac, meclofenamate, meloxicam, nabumetone, naproxen, naproxen indomethacin, oxaprozin, piroxicam, salsalate, sulindac, tolmetin, and valdecoxib.

The medical device of the present disclosure, e.g., a ureteral stent, may be manufactured to contain and release one or more of these or other therapeutic agents. In addition to the drugs listed herein, pharmaceutically acceptable salts, esters, and other derivatives of the drugs can also be utilized. The drugs provided herein can be loaded, for example, into a polymeric component of the medical device. When the medical device is a stent, the drug may be incorporated into the coil, a knitted construct that adjoins the coil, or a coating which impregnates the knitted construct. The drug may be incorporated into a coating which is coated onto the medical device.

Urologically beneficial drugs may be may be associated with the drug releasing stent in various ways, including the following, among others: (a) loaded in the interior (bulk) of a stent component, e.g., the monofilmant coil, or a multi-filament knitted construct, or a coating or sleeve or sheath, (b) bound to a surface of the stent, such as a surface of the monofilament coil, or the surface of the multifilament knitted construct, or the surface of a containment layer or a sleeve or sheath, where the drug is bound to the surface by any of covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating that covers all or a portion of the stent or a component thereof, (d) loaded in surface features (e.g., depressions) of the stent or a component thereof, and (e) combinations of the forgoing.

The amount of urologically beneficial drug(s) associated with the drug-releasing stent should be a therapeutically or prophylactically effective amount, where that amount may range, for example, from than 1 wt % or less to 2 wt % to 5 wt % to 10 wt % to 25 wt % to 50 wt % or more, depending the particular drug and the desired effect.

In one embodiment of a medical device including a drug, the present disclosure provides a medical device for placement in a body of a mammal, comprising: a polymeric matrix forming the device and defining a lumen through the device, the matrix comprising polymer macromolecules and defining spaces between the polymer macromolecules; a drug contained within at least some of the spaces of the matrix; and a material contained within at least some of the spaces of the matrix to affect diffusion of the drug out of the polymeric matrix when the medical device is placed in the body of the mammal. Optionally, one or more of the following may further characterize a medical device of the present disclosure: each of the polymeric material and the drug has a molecular weight where the molecular weight of the drug is less than the molecular weight of the polymeric material; the quantity of drug associated with the device is between 0.1 and 50 weight percent of the weight of the device; the medical device is a ureteral stent or a catheter; the polymeric component comprises ethylene vinyl acetate (EVA); the polymeric component is hydrophobic; at least some of the spaces that contain the drug also contain polymeric material; the drug comprises oxybutynin chloride or ketorolac; the material in association with the drug comprises polyethylene glycol (PEG); the drug is in association with a biodegradable material; the drug is in association with a material from which the drug must dissociate before diffusing out of the polymeric matrix; the polymeric matrix is coated onto the device.

Thus, the medical device can be used as a vehicle to deliver one or more drugs to the body of a patient. A ureteral stent, catheter, and/or other medical device can be used to deliver the drug(s) by placing the device entirely or partially in the body of a patient. By using certain material(s) and drug(s) in a polymeric matrix, the diffusion of the drug(s) out of the matrix can be controlled in ways previously unachievable. One or more drugs may thereby be administered to the patient's body over a sustained time (ranging from days to months, for example) and at a relatively constant, and therapeutic, level.

A drug-delivering medical device according to the present disclosure may be formed entirely or partially of a polymeric matrix, loaded with the drug(s) and material(s) that affect the diffusion of the drug(s) out of the matrix when the device is placed in the body of a human or other mammal. The device can be a ureteral stent, a catheter, a dialysis tube, a cannula, a urethral stent, a suture, or other medical device designed for placement (entirely or partially) in the body. A device according to the present disclosure may optionally be coated entirely or partially with such a loaded polymeric matrix. For example, a hydrophobic polymeric matrix can coat all or some portion of a lead wire, a stent, or a catheter.

In another embodiment, the present disclosure provides a ureteral stent comprising an elongated stent body, a deployable retention structure, and a drug-releasing member selected from (i) a sleeve of drug-releasing material that is disposed over at least a portion of the deployable retention structure, (ii) a sheet of drug-releasing material that is attached to the deployable retention structure and (iii) a sheet of drug-releasing material connected to a sleeve of material that is disposed over at least a portion of the deployable retention structure. Optionally, one or more of the following features may further describe this drug-releasing ureteral stent: a sleeve of drug-releasing material is disposed over at least a portion of the deployable retention structure, where optionally the sleeve is a biodisintegrable sleeve and/or the sleeve is a heat shrinkable sleeve and/or the sleeve ranges from 1 to 4 mm in inner diameter, from 2 to 500 mm in length and from 50 to 200 micrometers in thickness; the stent comprises a sheet of drug-releasing material that is attached to the deployable retention structure, where optionally, the sheet is a biodisintegrable sheet and/or the sheet is an elastic sheet and/or the sheet ranges from 2 to 20 mm in width, from 2 to 500 mm in length and from 50 to 200 micrometers in thickness; the stent includes a retention structure in the form of a coil or a loop and wherein the sheet of drug-releasing material spans a majority of the coil or loop area upon deployment of the retention structure; the stent includes a sheet of drug-releasing material connected to a sleeve of material that is disposed over at least a portion of the deployable retention structure; the stent includes a retention structure which is a kidney retention structure configured to be delivered through the ureter and deployed in the kidney, where optionally the retention structure is adapted to be reduced to a profile that is sufficiently small during deployment to allow the retention structure to be delivered to the kidney; the stent has a retention structure that comprises a plurality of elongated elements to which the sheet of drug-releasing material is attached and between which the sheet of drug-releasing material is situated upon deployment of the retention structure; the stent body and deployable retention structure comprise a biostable polymer.

Loading of the drug into the polymer may be between about 0 to 20 weight percent of the device depending on the nature of the material, the quantity of the polymer, the release profile of the polymer, the release profile of the drug, the desired drug diffusion effect, and the desired period for drug delivery, among other factors. In one embodiment, loading of the drug is between about 1 to 10 weight percent of the device.

Materials may be added to the polymer composition specifically to influence the release of the drug from the polymer. Such materials include, without limitation, styrenethylene-butylene-styrene (SIBS), collagen, alginates, carboxymethyl cellulose (CMC), hydroxypropyl cellulose (HPC), dextrin, plasticizers, lipophilic material and other fatty acid salts, pore formers, sugar, glucose, starch, hyaluronic acid (HA), chelating agents, including ethylenediaminetetraacetic acid (EDTA), polyethylene glycol (PEG), polyethylene oxide (PEO), and copolymers thereof. Multiple materials of varying release profiles may be incorporated within the polymeric composition with the drug(s) to achieve the desired drug release profile.

In one aspect, the present disclosure provides a bioabsorbable medical implant that is at least partially covered by an outer containment layer, where the containment layer is either nonbioabsorbable, or is at least partially bioabsorbable but does not degrade as quickly as does the medical implant. In one embodiment, in vivo, the medical implant will degrade into pieces while the outer layer retains sufficient structural integrity to provide a barrier which cannot be crossed by the pieces from the implant. In this way, the pieces are constrained to staying in a localized area where they cannot cause any harm to the host. In fact, even as the pieces degrade, the resulting smaller pieces and ultimately the molecular components of the implant, will all stay within the outer containment layer, and together may be conducted to a place that is safe for elimination.

Optionally, the containment layer and the degraded medical device are simultaneously eliminated. Both the medical device and the containment layer may become soft and compliant, and may travel along the tube into which they were implanted, e.g., the ureter until they are simultaneously eliminated from the host. The containment layer may be degradable, however it need not be degradable. So long as the containment layer becomes soft and flexible, and maintains its integrity, it may be eliminated from the host at the same time that the medical device is eliminated.

The containment layer may assist in managing the segmentation of the device, i.e., the disintegration of the device into pieces. The containment layer may, for example, be located over regions of the device and protect those regions from contact with the host's fluids. The unprotected regions will degrade more quickly, and may lead to breaks or segments in the medical device. The containment layer may be porous, and so allow a controlled amount of the host's surrounding fluid to contact the medical device. By adjusting the porosity of the containment layer, the segmentation of the device may be managed. As another option, by using a gradient coating, the parts of the medical device covered by the relatively thinner (less coating) regions will break into segments first. As another option, the medical device may be pre-degraded by, e.g., exposing selected portions of the device to moisture for some period of time. These pre-selected regions may prematurely degrade, relative to other parts of the medical device. In this case, the containment layer may be located over the pre-degraded regions, to control when those regions are exposed to the host's fluids.

While the containment layer may be present on the outside of the medical device, an alternative embodiment places the containment layer on the inside of a medical device, for example, on the inside of a medical device which has a hollow space, i.e., a lumen. An exemplary medical device which has a lumen is a stent. When a containment layer is placed on the inside of the stent, and the stent is biodegradable, then the pieces of stent that form during stent degradation are held between the containment layer and the tissue of the host, for a sufficient time that the pieces become manageable small, that is, they are not of a size that is harmful to the host, or alternatively the pieces degrade into their component polymeric or monomeric components and can migrate through the containment layer.

Gradients

In one aspect, the medical device is characterized as having a gradient. A gradient refers to variation in some property, e.g., composition, of the medical device as a function of a direction. This gradient provides for variation in degradation along the gradient. For example, the average molecular weight of the polymer that forms the medical device may vary along a direction of the medical device, such that the polymer at the distal end of the medical device or a portion thereof has a higher average molecular weight than does the polymer at a proximal end of the medical device or a portion thereof. In this way, the proximal end of the medical device or portion thereof may degrade more rapidly than does the distal end where the polymer has a higher initial average molecular weight. The provision of a gradient in the medical devices of the present disclosure provides a mechanism for managed degradation of the device. In one embodiment, the gradient does not impact or effect the functionality of the medical device, but only impacts the degradation profile of the device. Such nonhomogeneity in the medical device may be referred to herein as the gradient of the medical device, and a medical device having such a gradient may be referred to as a graduated medical device.

Optionally, a containment layer of the present disclosure may be characterized in terms of having a gradient, such that the containment layer that covers one portion of a medical device is different from the containment layer that covers another portion of the medical device. Such nonhomogeneity in the containment layer will be referred to herein as the gradient in the containment layer, and the containment layer having such a gradient may be referred to as a graduated containment layer.

For example, in one embodiment gradients provide different degradation rates. Gradients may be constructed such that the containment layer covering one portion of a medical device degrades at a different rate, either faster or slower, than does the containment layer covering a different portion of the medical device.

As another example, in another embodiment gradients provide different degrees of degradation. Thus, gradients may be constructed such that the containment layer covering one portion of the medical device will degrade to a different extent than does the containment layer covering a different portion of the medical device. The extent of degradation may be measured in different ways. For instance, the thickness of the containment layer may be measured before implantation and then after it has been implanted and degraded to the fullest extent that it will degrade. The change in thickness may be described as a percentage reduction in thickness, where the gradient provides for a different percentage reduction in thickness over one portion of the medical device, either greater or less, compared to the reduction in thickness that occurs over a different portion of the medical device.

As yet another example, in one embodiment the gradient provides different sized holes in the containment layer at different locations, or optionally holes in one location but no holes in another location of the containment layer. In other words, the containment layer may have variation in porosity. Thus, the gradients may be constructed such that the containment layer over one portion of the medical device is in the form of a mesh, net, weave or other construct that includes holes, while the containment layer over a different portion of the medical device is solid, i.e., does not have any holes. Alternatively, the gradients may be constructed such that containment layer over one portion of the medical device is in the form of a mesh etc. with relatively large holes, while the containment layer over a different portion of the medical device is also I the form of a mesh etc. but with relatively smaller holes.

Gradients may be formed in various ways. For example, different compositions, having different degradation rates, may be used to form the containment layer over different portions of the medical device. Thus, a composition having a relatively high degradation rate may be placed over a first portion of a medical device while a composition having a relatively slower degradation rate maybe placed over a second portion of the medical device. In this way, the containment layer will degrade more quickly in some places than in other places.

As another example, a single composition may be used to form a graduated containment layer. For instance, a single composition may be coated to a first thickness over a first portion of a medical device while the same composition is used to create a coating having a second thickness over a second portion of the medical device. In general, a thicker coating will be retained for a longer time on the medical device than will a thinner coating, or in other words, a thicker coating will degrade more slowly than a thinner coating, all other factors being equal. A thicker coating may be formed, for example, by repeatedly coating a region of the containment layer where greater coating thickness is desired.

The thickness of the containment layer may vary throughout the medical implant. However, at its thickest point, in various embodiments, the containment layer has a thickness of greater than 10 microns, or greater than 20 microns, or greater than 30 microns, or greater than 40 microns, or greater than 50 microns, or greater than 60 microns, or greater than 70 microns, or greater than 80 microns, or greater than 90 microns, or greater than 100 microns, or greater than 110 microns, or greater than 120 microns, or greater than 130 microns, or greater than 140 microns, or greater than 150 microns, or greater than 160 microns, or greater than 170 microns, or greater than 180 microns, or greater than 190 microns, or greater than 200 microns. The maximum thickness may be 500 microns, or 400 microns, or 300 microns, or 200 microns, or 150 microns, or 100 microns. As mentioned previously, the containment layer may be a coating, where the thickness of the coating at its thickest part is any of the aforementioned thicknesses.

The amount of the containment layer may vary throughout the medical implant. In one aspect, in addition to or instead of specifying a thickness for a containment layer, the containment layer may be characterized in terms of how much organic polymer is present over a given volume of medical device. For example, the amount may be specified in terms of mg organic polymer per square centimeter ($cm^2$) of medical device. In various embodiments, the medical device is covered with containment layer in the amount of at least 10 $mg/cm^2$; or at least 15 $mg/cm^2$; or at least 20 $mg/cm^2$; or at least 25 $mg/cm^2$; or at least 30 $mg/cm^2$; or at least 35 $mg/cm^2$; or at least 40 $mg/cm^2$; or at least 45 $mg/cm^2$; or at least 50 $mg/cm^2$.

As yet another example, the filaments that form a weave may be woven tighter or looser in order to effect the number and size of the holes in the weave. A containment layer may be constructed from two or more different weaves, providing larger holes over a first portion of a medical device and smaller holes over a second portion of the medical device. In this way, the containment layer will allow the underlying medical device to degrade more quickly in the first portion of the medical device (where the mesh hole sizes are larger and so the mesh affords more access of the surrounding body fluids to the medical device) and more slowly in the second portion of the medical device (where the mesh hole sizes are smaller).

Thus, in one embodiment the present disclosure provides a medical implant comprising a medical device and a graduated containment layer that covers at least a portion of the medical device. Optionally, the graduated containment layer may comprise multiple thicknesses, e.g., 2, 3, 4, 5, or more than 5 different thicknesses at different locations. The graduated containment layer having multiple thicknesses at different locations may be formed by having various numbers of coating layers of a polymer composition at different locations, and thus may be said to comprise multiple layers (of coating composition). Also optionally, the graduated containment layer may comprise multiple compositions, e.g., 2, 3, 4, 5, or more than 5 different compositions at different locations. Optionally, the graduated containment layer may comprise variation in two or more properties, e.g., multiple thicknesses and multiple compositions.

While thickness, composition and porosity are examples of variation that may be present in a containment layer, these are exemplary only. Other variations can also be used to create a graduated containment layer according to the present disclosure, for example, variation in texture, variation in hydrophilicity, variation in thermal stability, variation in tensile strength, and variation in fiber density when the containment layer contains fibers, to name a few.

In one embodiment, the containment layer is made from one or more organic polymers. The containment layer may be completely non-biodegradable. However, in another embodiment, the containment layer is biodegradable, but it degrades at a slower rate than the medical device. In this way, if the medical device is degrading into pieces, the containment layer retains its structural integrity and holds the pieces together within a confined space, for a time sufficient for the pieces to degrade into even smaller pieces that are not harmful to the host, and/or into the polymeric and/or monomeric components of the medical device.

In one embodiment, the containment layer is a coating on the medical device. The coating may be present on all of the exposed surfaces of the medical device, or only one some of those surfaces, e.g., the sides. The coating may be completely non-biodegradable. However, in another embodiment, the coating is biodegradable, but it degrades at a slower rate than the medical device. In this way, if the medical device is degrading into pieces, the coating retains its structural integrity and holds the pieces together within a confined space, for a time sufficient for the pieces to degrade into even smaller pieces that are not harmful to the host, and/or into the polymeric and/or monomeric components of the medical device.

Particularly when the coating is biodegradable, and the medical device is disintegrating into pieces, the coating must maintain sufficient strength during the period of time when the medical device disintegrates, such that the coating will be able to contain the pieces within the coating. To provide this function, the coating must be of adequate thickness. In order to provide a coating of adequate thickness, the medical device may be dipped into a polymer solution, i.e., a solution of dissolved polymer. The device may be dipped multiple times into the solution, in order to build up a thickness of polymer that will maintain sufficient strength and integrity to function as a containment layer during the disintegration of the medical device. Alternatively, the medical device may be drawn through a polymer solution. The rate at which the device is drawn through the solution will impact the thickness of the coating: a slower draw rate will provide for a thicker coating.

When a polymer solution is used to form the coating on the medical device, the concentration of polymer in the solution is also a factor that must be considered. A higher concentration of polymer will tend to deposit more polymer on the surface of the medical device, when that device is dipped, drawn, or otherwise coated with the polymer so as to form a containment layer.

The containment layer is placed on those portions of the medical device where it is desired to protect the host from damage or injury or trauma due to pieces of the device being formed during biodegradation. For example, in the case of a stent which is implanted into a host, where the stent is implanted partially within the host's kidney and partially outside of the kidney, it will be desirable that pieces of disintegrating stent not disperse in kidney and give rise to kidney stones. Accordingly, the portion of the stent that will be implanted within the kidney may be coated, while the portion of the stent that is implanted outside of the kidney may not be coated. In this way, a containment layer is present on only a portion of the medical device.

The present disclosure provides that any medical device that degrades by a disintegration process, i.e., by a process whereby the device breaks down into pieces, may be provided with a containment layer. An exemplary device of this type is an endoureteral stent. The stent is biodegradable and disintegratable so that it initially maintains optimum ureteral patency for a predetermined period of time. However, at the conclusion of this period, the stent will begin to disintegrate into small pieces. In order to preclude those small pieces from traveling, the stent is at least partially encased by a containment layer. The layer retains sufficient integrity such that, during the period of time during which the small pieces are formed and then either degrade into non-harmful pieces, or degrade into their polymeric or molecular components, the containment layer will contain those small pieces. The containment layer thus acts to protect the host from the small pieces that are formed upon disintegration of the stent. The containment layer also protects the host from contact with rigid pieces which are not easily passed out of the body.

Optionally, the device may not break into smaller pieces, but may instead soften to such a degree that it may pass through the conduit in which it was implanted, e.g., the ureter.

In one embodiment, the present disclosure provides ureteral stents which have a diversity of properties at different locations of the stent, but the stent and components thereof are not assembled from multiple segments. Rather, the stent is assembled from a single uniform construct, and that construct is then modified to provide a diversity of properties at different locations of the construct. The diversity may in one or more properties including biodegradability, radiopacity, stiffness or flexibility, and loading with therapeutic agents. The diversity is created by methods as disclosed herein, e.g., by cutting a slit in a component of the stent, by selectively degrading the stent or a component thereof before it is implant into the host, and other methods disclosed herein.

In one embodiment, the medical device is a stent, and the stent is a construct of a fiber-reinforced elastomeric film designed with at least one position-retaining end, wherein the fiber-reinforcement is (a) a combination of a monofilament coil and weft-knitted tube multifilament yarn; (b) a combination of monofilament coil and a braided multifilament yarn; (c) a tube comprising a braided or weft-knitted monofilament yarn; or (d) a weft-knitted or braided monofilament yarn in the form of a tube.

In still another embodiment, the stent is a construct of a fiber-reinforced elastomeric film designed with at least one position-retaining end wherein the fiber reinforcement is a combination of a monofilament and knitted or braided multifilament yarn, wherein the fiber reinforced elastomeric film is in the form of a tube with a central, main component having a smaller diameter than that of the patient ureter wherein each of the position-retaining ends defines two freely laterally deformable components formed of initially partially overlapping bitubular ends of the main, central component and a laterally fused tube which are radially and axially cut to produce two over-extended flaps attached to an intact semi-cylindrical extension of the main, central tube.

In yet still another embodiment, the stent is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a tube with a smaller diameter than that of the patient ureter and having at least one position-retaining end, wherein the position-retaining end is an angled portion of the main tube having a length comparable to the patient ureter and comprising a flexible hinge that maintains an angle of more than 30 degrees with respect to the main tube in an absence of deforming stress.

In another embodiment, the stent comprises a retention portion configured to help retain the stent in place within a body of a patient; and an elongate portion extending from the retention portion, the elongate portion having a sidewall defining a lumen, the sidewall having a first section and second section, the first section of the sidewall having a first thickness, the second section of the sidewall having a second thickness different than the first thickness. Optionally, the stent may be further characterized by one or more of the following: the retention portion is configured to be disposed within a kidney of the patient; the retention portion is a first retention portion and the stent further comprises a second retention portion configured to help retain the stent in place within the body of the patient; the first section of the sidewall forms an annular ring; the first section of the sidewall forms a spiral; the first section of the sidewall forms a dimple; the sidewall has a third portion, the second portion of the sidewall being disposed between the first portion of the sidewall and the third portion of the sidewall; the sidewall has a third portion, the third portion has a thickness different than the second thickness, the second portion of the sidewall being disposed between the first portion of the sidewall and the third portion of the sidewall; the sidewall has a third portion, the second portion of the sidewall being disposed between the first portion of the sidewall and the third portion of the sidewall, the third portion having a third thickness, the second thickness being greater than the first thickness, the second thickness being greater than the third thickness; the first portion of the sidewall has a first section and a second section, the first section of the first portion forming a spiral rotating in a first direction, the second section of the first portion forming a spiral rotating in a second direction different than the first direction. This stent, including optional embodiments thereof, may be modified by techniques disclosed herein to display managed degradation when the stent is located within a host. For instance, a slit may be made in the slit to provide a site that promotes degradation.

In another embodiment the stent comprises a retention portion configured to help retain the stent in place within a body of a patient; and an elongate portion extending from the retention portion, the elongate portion having a first member and a second member, the first member being devoid of a lumen, the second member being devoid of a lumen, the first member and the second member being intertwined. In another embodiment, the stent comprises a retention portion configured to help retain the stent in place within a body of a patient; and an elongate portion extending from the retention portion and having an expanded configuration and a nominal configuration, the elongate portion having a sidewall defining a lumen extending from a first end portion of the elongate portion to a second end portion of the elongate portion, the sidewall defining a chamber, the chamber being configured to receive a fluid to place the elongate portion in its expanded configuration. Again, either of these stents may be modified by techniques disclosed herein to demonstrate managed degradation with situated within a host.

In another embodiment, the stent is a construct of a fiber-reinforced elastomeric film designed with at least one position-retaining end wherein the fiber reinforcement is a combination of a monofilament and knitted or braided multifilament yarn, wherein the fiber-reinforced film is tubular with a central main component having a smaller diameter than that of the patient ureter and comprising at least one position-retaining end wherein the position-retaining end is a highly flexible extension of the central main tube, acquiring a goose-neck shape after insertion in the patient ureter but can be made co-linear with the central main tube during insertion with an applicator.

In another embodiment, the stent comprises an elongate member having a first portion and a second portion, the second portion having a sidewall that defines a single lumen, the first portion being coupled to the second portion, the first portion configured to be disposed within a kidney of a patient, the sidewall of the second portion of the elongate member is configured to deliver fluid from a first location of the sidewall of the second portion to a second location of the sidewall of the second portion via at least one of capillary action and wicking, the second portion of the elongate member configured to be disposed within at least one of a bladder of a patient and a ureter of the patient, at least a portion of the first portion being disposed within the lumen. Optionally, one or more of the following features may further characterize this stent: the second portion of the elongate member is constructed of a multi-stranded material; the second portion of the elongate member is constructed of a yarn; the second portion of the elongate member has a configuration selected from a group consisting of a braided tube configuration and a long woven strip configuration; the second portion of the elongate member is constructed of a melt spun polypropylene with a high loading of barium sulphate; the stent further comprises a proximal retention structure configured to be disposed within the bladder of a patient, the proximal retention structure being coupled to the second portion of the elongate member; the stent further comprises a distal retention structure configured to be disposed within the kidney of the patent, the distal retention structure being coupled to the first portion of the elongate member; the first portion is coupled to the second portion via an interference fit; the second portion of the elongate member has a substantially solid tubular shape; the second portion of the elongate member is substantially flexible; the first portion of the elongate member is substantially rigid; the second portion of the elongate member is more flexible than the first portion of the elongate member. This stent, including optional embodiments thereof, may be modified to demonstrate managed degradation according to the present disclosure.

In another embodiment, the medical device is a ureteral stent comprising: an elongate member having a first portion and a second portion, the second portion having a substantially solid cylindrical shape, the first portion being coupled to the second portion, the first portion configured to be disposed within a kidney of a patient, the first portion having a length such that the first portion terminates in at least one of the kidney and ureter of the patient, the second portion of the elongate member configured to deliver fluid from a first location of the second portion to a second location of the second portion via at least one of capillary action and wicking, the second portion of the elongate member configured to be disposed within at least one of a bladder of a patient and the ureter of the patient. This stent may be modified to demonstrate managed degradation according to the present disclosure.

In another embodiment, the stent contains at least one filament, where this filament has a longitudinal axis and is formed from materials including a bioabsorbable polymeric material. Polymer molecules within the bioabsorbable polymeric material may have a helical orientation which is aligned with respect to the longitudinal axis of the filament. The stent is at least partially bioabsorbed by a patient upon implantation or insertion of the stent into the patient. For example, the stent may comprise: a braided or woven configuration; a flared end portion at one of a proximal end or a distal end of the stent; and at least one filament having a longitudinal axis and comprising an oriented bioabsorbable polymeric material, wherein polymer molecules within the bioabsorbable polymeric material have a helical orientation which is aligned with respect to the longitudinal axis of the at least one filament. Optionally, one or more of the following may further describe the stent: the proximal end and the distal end comprise the flared end portion; the at least one filament is helically wound along at least a portion of a length of the stent; the stent comprises a plurality of the filaments, where optionally the plurality of the filaments are helically wound along at least a portion of a length of the stent, and where further optionally a first portion of the plurality of the filaments are helically wound in a first direction and a second portion of the plurality of the filaments are helically wound in an opposite direction to the first direction; the plurality of the filaments are braided and helically wound along at least a portion of the length of the stent; the stent comprises filaments of stainless steel or nitinol; the stent comprises between 12 and 36 helical filaments; where optionally between 6 and 18 filaments are in the form of helices, and are axially displaced in relation to each and wherein the helices extend in a first direction, and wherein an equal number of filaments comprise helices that extend a second direction that is opposite the first direction, the filaments are uniformly arranged about a longitudinal axis of the stent; the oriented bioabsorbable polymeric material comprises a single bioabsorbable polymer or a blend of bioabsorbable polymers; the oriented bioabsorbable polymeric material comprises a polymer selected from poly($\alpha$-hydroxy acid) homopolymers, poly($\alpha$-hydroxy acid) copolymers and blends thereof; the oriented bioabsorbable polymeric material comprises a polymer selected from polyglycolide, poly-L-lactide, poly-D-lactide, poly-DL-lactide, and blends thereof; the oriented bioabsorbable polymeric material has a crystallinity ranging from 0.1 to 20%; at least one filament comprises a core of the oriented bioabsorbable polymeric material; at least one filament comprises a coating of the oriented bioabsorbable polymeric material; the stent comprises a plurality of oriented filaments that are arranged to form a pattern of geometric diamond-shaped cells; a plurality of filaments are wrapped about one another to form interlocking joints; at least one filament comprises a therapeutic agent; and the stent is selected from a coronary vascular stent, a peripheral vascular stent, a urethral stent, a ureteral stent, a biliary stent, a tracheal stent, a gastrointestinal stent and an esophageal stent.

Another optional embodiment provides a stent which is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a tube having at least one position-retaining end, wherein the retaining end is an inverted cone having a diameter at the wider cross-section exceeding that of the main tube and that can be reversibly compressed to conform with the main tube diameter, which is also smaller than that of the patient ureter, upon applying radial compressive force in an applicator. It is preferred that the inverted cone is partially slit, yielding a cone wall having at least two leaflets and preferably three to five leaflets to facilitate the radial compression upon insertion with an applicator.

Yet another optional embodiment provides a which is a construct of a fiber-reinforced elastomeric film designed with at least one position-retaining end wherein the fiber reinforcement is a combination of a monofilament and knitted or braided multifilament yarn, wherein the elastomeric film is tubular with a central main component having a smaller diameter than that of the patient ureter and with at least one position-retaining end wherein the position-retaining end is an asymmetrically inverted cone with a teardrop cross-section, slit axially, at the peak of the teardrop which has an average diameter at the wider cross-section exceeding that of the central main tube wherein the slit asymmetric cone can be reversibly compressed to conform with the central main tube diameter upon applying radial compressive force in an applicator.

In yet another optional embodiment, the stent is a construct of a fiber-reinforced elastomeric film, wherein the fiber-reinforcement is a monofilament yarn or a combination with knitted or braided multifilament yarn, wherein the reinforced elastomeric film is tubular with a central main component that is a unilaterally, longitudinally crimped, inflatable tube having a circular cross-section that is smaller than that of the patient ureter when outwardly expanded, and having at least one position-retaining end wherein the position-retaining end is a unilaterally crimped, inflatable, asymmetric, inverted cone having a teardrop cross-sectional geometry and a crimp at the peak of the teardrop that is collinear with the crimp of the central main tube, wherein the average diameter of the inverted cone, when outwardly expanded, exceeds that of the central main tube.

Optionally, the fiber-reinforced elastomeric film is formed of a segmented copolymer made from a polyethylene glycol and at least one cyclic monomer selected from the group represented by l-lactide, epsilon-caprolactone, trimethylene carbonate, glycolide, a morpholine-dione, p-dioxanone, and 1,5-dioxapan-2-one. Optionally, the film is formed from a mixture of epsilon-caprolactone and glycolide. Optionally, the film is formed from a mixture of L-lactide and glycolide. An exemplary composition of an elastomeric swellable film composition is a crystalline copolymer of a high molecular weight (20-35 kDa) polyethylene glycol (PEG) and 95/5 (molar) mixture of epsilon-caprolactone/glycolide, wherein the weight percent of the PEG component in the copolymer is about 10 percent.

Another exemplary composition of an elastomeric film composition is a crystalline segmented copolymer made in two steps. The first step entails the formation of an amorphous or low melting copolymer made from epsilon-caprolactone, trimethylene carbonate and glycolide by polymerization in the presence of triethanolamine and stannous octanoate as the initiator and catalyst, respectively. In the second step, the product of the first step is reacted with a mixture of l-lactide and epsilon-caprolactone to produce a crystalline triaxial final copolymer.

Optionally, a film may be prepared from electrospun fibers. Also optionally, a fiber-reinforced film may comprise or contain a monofilament yarn, optionally in combination with knitted or braided multifilament yarn, wherein the reinforcing monofilament yarn is formed of a segmented copolymer made from at least two cyclic monomers selected from the group represented by l-lactide, epsilon-caprolactone, trimethylene carbonate, glycolide, a morpholine-dione, p-dioxanone, and 1,5-dioxapan-2-one. Optionally, it is formed from l-lactide, epsilon-caprolactone, and trimethylene carbonate which is a relatively slowly degrading composition. Optionally, it is formed from glycolide, epsilon-caprolactone, and trimethylene carbonate which is a relatively quickly degrading composition.

The reinforcing monofilament yarn may also be a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, epsilon-caprolactone, trimethylene carbonate, glycolide, p-dioxanone, 1,5-dioxepan-2-one, and a morpholinedione. Furthermore, the reinforcing monofilament yarn can be a composite of an inorganic microparticulate dispersed phase of at least one material selected from the group consisting of barium sulfate, zirconium oxide, and absorbable phosphate glass and an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

In still yet another optional embodiment, the present disclosure provides a bioabsorbable and disintegratable, multicomponent, non-migrating endoureteral stent which is a construct of a fiber-reinforced elastomeric film designed with at least one position-retaining end, wherein the fiber-reinforcement is a monofilament yarn or a combination with knitted multifilament or braided yarn, wherein the reinforcing knitted or braided multifilament fabric is formed of a crystalline segmented copolymer. An exemplary composition of such copolymer is a triaxial copolymer made in two steps. The first step entails the formation of an amorphous or low melting triaxial prepolymer using epsilon-caprolactone and/or trimethylene carbonate in the presence of trimethylolpropane and stannous octanoate as the initiator and catalyst, respectively. In the second step, the product of the first step is reacted with glycolide or a mixture of glycolide with epsilon-caprolactone and/or trimethylene carbonate. Another exemplary composition is a copolymer for use in producing knitted or braided multifilament yarn, which is a crystalline copolymer made from a polyethylene glycol and at least one cyclic monomer selected from the group represented by l-lactide, ε-caprolactone; trimethylene carbonate, glycolide, a morpholine-dione, p-dioxanone, and 1,5-dioxapan-2-one, but preferably from a polyethylene glycol, l-lactide, and trimethylene carbonate, and more preferably from a segmented copolymer of l-lactide and trimethylene carbonate. Optionally, the copolymer is made from glycolide and trimethylene carbonate, which provides a relative fast degradation profile for the yarn.

Thus, in one embodiment the present invention provides an absorbable and disintegratable, multicomponent, non-migrating endoureteral stent which is a construct of a fiber-reinforced elastomeric film designed with at least one position-retaining end, wherein the fiber-reinforcement is a combination of a monofilament coil and a braided multifilament yarn, and wherein the film is formed of a crystalline segmented copolymer made from a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione. The film may also be formed from a crystalline segmented copolymer made from l-lactide and at least one cyclic monomer selected from the group consisting of glycolide, ε-caprolactone, trimethylene carbonate, p-dioxanone and 1,5-dioxepan-2-one, and a morpholinedione.

In addition, the present disclosure provides an absorbable and disintegratable multicomponent, non-migrating endoureteral stent which is a construct of a fiber-reinforced elastomeric film designed with at least one position-retaining end, wherein the fiber-reinforcement is a combination of a monofilament coil and a braided multifilament yarn, and wherein the reinforcing monofilament yarn is formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing monofilament yarn is a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, p-dioxanone, 1,5-dioxepan-2-one, and a morpholinedione. The reinforcing monofilament yarn can also be a composite of an inorganic microparticulate dispersed phase of at least one material selected from the group of barium sulfate, zirconium oxide, and absorbable phosphate glass and an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

Thus the present disclosure also provides an optional embodiment which is an absorbable and disintegratable multicomponent, non-migrating endoureteral stent which is a construct of a fiber-reinforced elastomeric film designed with at least one position-retaining end, wherein the fiber-reinforcement is a combination of a monofilament coil and a braided multifilament yarn, and wherein the reinforcing braided multifilament fabric is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one. Alternatively, the reinforcing braided multifilament tube is formed from a crystalline segmented copolymer of l-lactide and at least one cyclic monomer selected from the group consisting of glycolide, ε-caprolactone, trimethylene carbonate, p-dioxanone, 1,5-dioxepan-2-one, and a morpholinedione.

In another embodiment, the present disclosure provides that the stent is a construct of a fiber-reinforced elastomeric film designed with at least one position-retaining end, wherein the fiber-reinforcement is a tube of a braided or weft-knitted monofilament yarn, and wherein the fiber-reinforced film is tubular with a central main component having a smaller diameter than that of the patient ureter and having at least one position-retaining end, and wherein the position-retaining end is a highly flexible extension of the central main tube, acquiring a loop shape with an open end parallel to the axis of the central main tube after insertion in the patient ureter and the loop can be made co-linear with the central main tube during insertion with an applicator. The film component of the assembled stent is formed of a crystalline segmented copolymer made from a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione. Alternatively, the film is formed of a crystalline segmented copolymer made from l-lactide and at least one cyclic monomer selected from the group consisting of glycolide, ε-caprolactone, trimethylene carbonate, p-dioxanone and 1,5-dioxepan-2-one, and a morpholinedione.

In another embodiment, the present disclosure provides that the stent is a construct of a fiber-reinforced elastomeric film designed with at least one position-retaining end, wherein the fiber-reinforcement is a tube of a braided or weft-knitted monofilament yarn, and wherein the reinforcing braided or weft-knitted monofilament yarn is formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing braided or weft-knitted monofilament yarn is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one. The reinforcing weft-knitted or braided monofilament can also be a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. Furthermore, the reinforcing weft-knitted or braided monofilament can be a composite of an inorganic microparticulate dispersed phase of at least one material selected from the group of barium sulfate, zirconium oxide, and absorbable phosphate glass and an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

Optionally, the stent is a construct of a fiber-reinforced elastomeric film designed with at least one position-retaining end, wherein the fiber reinforcement is a weft-knitted or braided monofilament scaffold and the reinforced construct therefrom is in the form of a tube comprising a central main component having a diameter smaller than that of the patient ureter and at least one position-retaining end, wherein the position-retaining end is an inverted cone having a series of diameters designed to provide progressively wider cross-sections than that of the central main tube and can be reversibly compressed to conform radially with the central main tube upon applying radial compressive force during insertion to the urogenital tract using a tubular applicator, and wherein the film is formed of a crystalline segmented copolymer made from a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione. Alternatively, the film is formed of a crystalline segmented copolymer made from l-lactide and at least one cyclic monomer selected from the group consisting of glycolide, ε-caprolactone, trimethylene carbonate, p-dioxanone and 1,5-dioxepan-2-one, and a morpholinedione. The reinforcing weft-knitted or braided monofilament yarn may optionally be formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing braided or weft-knitted monofilament yarn is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one.

In another optional embodiment, the stent is a construct of a fiber-reinforced elastomeric film designed with at least one position-retaining end, wherein the fiber reinforcement is a weft-knitted or braided monofilament scaffold and the reinforced construct therefrom is in the form of a tube comprising a central main component having a diameter smaller than that of the patient ureter and at least one position-retaining end, wherein the position-retaining end is an inverted cone having a series of diameters designed to provide progressively wider cross-sections than that of the central main tube and can be reversibly compressed to conform radially with the central main tube upon applying radial compressive force during insertion to the urinogenital tract using a tubular applicator, and wherein the reinforcing weft-knitted or braided monofilament yarn is a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. Alternatively, the reinforcing braid or weft-knitted monofilament yarn is a composite of an inorganic microparticulate dispersed phase of at least one material selected from the group of barium sulfate, zirconium oxide, and absorbable phosphate glass, and wherein an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

In another embodiment, the present disclosure provides an absorbable and disintegratable, multicomponent, non-migrating endoureteral stent which is a construct of a fiber-reinforced elastomeric film designed with at least one position-retaining end, wherein the fiber reinforcement is a weft-knitted monofilament yarn and the reinforced construct is in the form of a tube with a central main component having a smaller diameter than that of the patient ureter and having at least one position-retaining end wherein the position-retaining end is a highly flexible extension of the central main tube, acquiring a loop shape with an open end parallel to the axis of the central main tube after insertion in the patient ureter and the loop can be made co-linear with the central main tube during insertion with an applicator, and wherein the film is formed of a crystalline segmented elastomeric high l-lactide copolymer and the monofilament is formed of a segmented l-lactide copolymer with at least one cyclic monomer selected from the group consisting of glycolide, ε-caprolactone and a morpholinedione, and wherein the monofilament contains a microparticulate inorganic filler selected from the group of barium sulfate, zirconium oxide, and an absorbable phosphate glass.

In one embodiment, the medical device is a stent comprising a filament which has a longitudinal axis and which comprises an oriented bioabsorbable polymeric material, wherein polymer molecules within the bioabsorbable polymeric material have a helical orientation which is aligned with respect to the longitudinal axis of the filament, and wherein the stent is at least partially bioabsorbed by a patient upon implantation or insertion of the stent into the patient. In optional embodiments, the following one or more features may further characterize the medical device: a) the filament is helically wound along at least a portion of the length of the stent; b) the stent comprises a plurality of said filaments, where optionally the plurality of filaments are helically wound along at least a portion of the length of the stent, optionally a plurality of the filaments are helically wound in a first direction and a plurality of the filaments are helically wound in an opposite direction; c) the filament is a braided filament; a plurality of the braided filaments are braided and helically wound along at least a portion of the length of the stent; d) the filament is a knitted filament; e) the plurality of filaments are knitted filaments; the orientated bioabsorbable polymeric material comprises either a single bioabsorbable polymer or a blend of bioabsorbable polymers; f) the oriented bioabsorbable polymeric material comprises a polymer selected from poly(alpha-hydroxy acid) homopolymers, poly(alpha-hydroxy acid) copolymers and blends thereof; g) the oriented bioabsorbable polymeric material comprises a polymer selected from polyglycolide, poly-L-lactide, poly- D-lactide, poly-DL-lactide, and blends thereof; h) the oriented bioabsorbable polymeric material has a crystallinity ranging from 0.1 to 20%; i) the filament comprises a core of oriented bioabsorbable polymeric material; j) the stent is selected from a coronary vascular stent, a peripheral vascular stent, a urethral stent, a ureteral stent, a biliary stent, a tracheal stent, a gastrointestinal stent and an esophageal stent.

Optionally, the stent is capable of maintaining patency and remaining at the application site for at least two days, or 2-3 weeks, or has degraded after 7 weeks, or has degraded after 90 days, or has degraded by four months.

The present disclosure provides the following additional exemplary embodiments:

In one embodiment, the medical device is a biodegradable endoureteral stent. The stent comprises a tubular elastomeric film and a tubular fiber reinforcement, where the tubular elastomeric film is a single tube covering the tubular fiber reinforcement. The stent has at least one position-retaining end and a central main tube having a smaller diameter than that of a patient ureter, wherein the at least one position-retaining end is an extension of the central main tube. The stent is configured to be positioned in the patient ureter and extend from a patient kidney to a patient bladder and to be retained in position by the at least one position-retaining end. The film reinforces and impregnates the fiber-reinforcement, wherein the fiber-reinforcement comprises a monofilament coil disposed over a knitted or braided tube of a monofilament or multifilament yarn. The film and fiber reinforcement each comprise an absorbable crystalline segmented copolymer comprising at least one cyclic monomer. The film and fiber reinforcement alone are capable of maintaining ureteral patency.

The following options may further define the stent: a) the at least one position-retaining end is a flexible extension of the central main tube, acquiring a goose-neck shape after insertion in the patient ureter but can be made colinear with the central main tube during insertion with an applicator; b) the tubular elastomeric film comprises a crystalline segmented copolymer of a polyethylene glycol and at least one cyclic monomer selected from the group consisting of l-lactide, epsilon-caprolactone, trimethylene carbonate, glycolide, p-dioxanone, 1,5-dioxepan-2-one, and a morpholinedione; c) the tubular elastomeric film comprises a crystalline segmented copolymer of l-lactide and at least one cyclic monomer selected from the group consisting of glycolide, ε-caprolactone, trimethylene carbonate, p-dioxanone and 1,5-dioxepan-2-one; d) the monofilament coil comprises a crystalline segmented copolymer of at least two cyclic monomers selected from the group consisting of l-lactide, ε-caprolactone, trimethylene carbonate, glycolide, a morpholinedione, p-dioxanone and 1,5-dioxepan-2-one; e) the monofilament coil comprises a composite comprising a polymeric matrix and an inorganic microparticulate dispersed phase contained within the matrix, the matrix comprising a crystalline segmented copolymer and the inorganic microparticulate dispersed phase comprising at least one material selected from the group consisting of barium sulfate, zirconium oxide, and absorbable phosphate glass; f) the monofilament coil comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; g) the monofilament coil comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione; h) the fiber-reinforcement comprises a monofilament coil and a braided tube of a multifilament yarn, where optionally, 1) the tubular elastomeric film comprises a crystalline segmented copolymer of polyethylene glycol and at least one cyclic monomer selected from the group consisting of l-lactide, ε-caprolactone, trimethylene carbonate, glycolide, p-dioxanone, 1,5-dioxepan-2-one, and a morpholinedione; 2) the tubular elastomeric film comprises a crystalline segmented copolymer of l-lactone and at least one cyclic monomer selected from the group consisting of glycolide, ε-caprolactone, trimethylene carbonate, p-dioxanone, and 1,5-dioxepan-2-one, and a morpholinedione; 3) the monofilament coil comprises a crystalline segmented copolymer of at least two cyclic monomers selected from the group consisting of l-lactide, epsilon-caprolactone, trimethylene carbonate, glycolide, a morpholinedione, p-dioxanone, 1,5-dioxepan-2-one; 4) the monofilament coil comprises a composite comprising a polymeric matrix and an inorganic microparticulate dispersed phase contained within the matrix, the matrix comprising a crystalline segmented copolymer of at least two cyclic monomers selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; 5) the monofilament coil comprises a composite comprising a polymeric matrix and an inorganic microparticulate dispersed phase contained within the matrix, the matrix comprising a crystalline segmented copolymer of a polyethylene glycol and at least two cyclic monomer selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; 6) the multifilament yarn comprises a crystalline segmented copolymer of a polyethylene glycol and at least one cyclic monomer selected from the group consisting of l-lactide, trimethylene carbonate, ε-caprolactone, glycolide, p-dioxanone, a morpholinedione and 1,5-dioxepan-2-one; 7) the multifilament yarn comprises a crystalline segmented copolymer of l-lactide and at least one cyclic monomer selected from the group consisting of glycolide, ε-caprolactone, trimethylene carbonate, p-dioxanone, 1,5-dioxepan-2-one and a morpholinedione; j) the monofilament coil is disposed over a tube of weft-knitted monofilament yarn, where optionally 1) the tubular elastomeric film comprises a crystalline segmented copolymer of polyethylene glycol and at least one cyclic monomer selected from the group consisting of l-lactide, ε-caprolactone, trimethylene carbonate, glycolide, p-dioxanone, 1,5-dioxepan-2-one, and a morpholinedione; 2) the tubular elastomeric film comprises a crystalline segmented copolymer of l-lactide and at least one cyclic monomer selected from the group consisting of glycolide, ε-caprolactone, trimethylene carbonate, p-dioxanone and 1,5-dioxepan-2-one, and a morpholinedione; 3) the monofilament yarn comprises a crystalline segmented copolymer of at least two cyclic monomers selected from the group consisting of l-lactide, ε-caprolactone, trimethylene carbonate, glycolide, a morpholinedione, p-dioxanone, and 1,5-dioxepan-2-one; 4) the monofilament yarn comprises a crystalline segmented copolymer of a polyethylene glycol and at least one cyclic monomer selected from the group consisting of l-lactide, trimethylene carbonate, ε-caprolactone, glycolide, p-dioxanone, a morpholinedione, and 1,5-dioxepan-2-one; 5) the monofilament yarn comprises a composite comprising a polymeric matrix and an inorganic microparticulate dispersed phase contained within the matrix, the matrix comprising a crystalline segmented copolymer of at least two cyclic monomers selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; and 6) the monofilament yarn comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; k) the stent is capable of maintaining patency and remaining at an application site for at least two days; l) the stent is capable of maintaining patency and remaining at an application site for two to four months; and m) the at least one position-retaining end contains at least 4 percent by weight of at least one powdered radiopacifier selected from the group consisting of barium sulfate, zirconium oxide, and bismuth subcarbonate.

The following are some additional the embodiments of the present disclosure:

1) A medical implant comprising a containment layer that at least partially encases a medical device, the medical device being at least partially biodegradable when the implant is implanted in a host, the containment layer being either nonbiodegradable or biodegradable, where the containment layer serves as a container for the medical device as that medical device degrades in vivo.
2) The implant of embodiment 1 wherein the device provides structural support within a host.
3) The implant of embodiments 1-2 wherein the device is a stent.
4) The implant of embodiments 1-3 wherein the stent is an endoureteral stent.
5) The implant of embodiments 1-4 wherein the containment layer is a coating on the implant.
6) The implant of embodiment 5 wherein the coating is hydrophilic.
7) The implant of embodiments 5-6 wherein the coating is biodegradable, but the coating degrades more slowly than the medical device.
8) The implant of embodiments 5-7 wherein the coating has a thickness of greater than 20 microns.
9) The implant of embodiments 5-8 wherein the coating has a thickness of greater than 40 microns.
10) The implant of embodiments 5-9 wherein the coating has a thickness of greater than 60 microns.
11) The implant of embodiments 5-10 wherein the coating has a thickness of greater than 80 microns.
12) The implant of embodiments 5-11 wherein the coating has a thickness of greater than 100 microns.
13) The implant of embodiments 5-12 wherein the coating has a thickness of greater than 120 microns.
14) A medical implant comprising a containment layer that is at least partially encased by a medical device, where the containment layer at least partially encases a hollow center of the medical device, the medical device being at least partially biodegradable when the implant is implanted in a host, the containment layer being either nonbiodegradable or biodegradable, where the containment layer provides a barrier between the degradation product that forms during the biodegradation of the medical device and the hollow space of the medical device.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Any of the medical device embodiments disclosed herein may include a drug, e.g., a therapeutic agent, or a prophylactic agent, as part of the medical device.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

In the description, certain specific details are set forth to provide a thorough understanding of various disclosed embodiments. However, one skilled in the relevant art will recognize that embodiments may be practiced without one or more of these specific details, or with other methods, components, materials, etc.

The Examples and preparations provided below further illustrate and exemplify the medical devices of the present invention and methods of preparing such devices. It is to be understood that the scope of the present invention is not limited in any way by the scope of the following Examples and preparations. In fact, unless the context indicates otherwise, when a specific polymer is used in an Example, this polymer is exemplary only and may, according to the present invention, be replaced with an alternative polymer. Also, when degradation times and properties are exemplified, it is to be understood that these values are approximations, and that other values would be obtained using different starting materials. The starting materials and various reactants utilized or referenced in the examples may be obtained from commercial sources, or are readily prepared from commercially available organic compounds, using methods well-known to one skilled in the art. Thus, the following examples are illustrative of embodiments of the invention, and are not to be construed as a limitation thereon.

EXAMPLES

Example 1

Preparation of Coil from MG5-B

A 1-liter stainless steel kettle with a 3-neck glass lid equipped with an overhead mechanical stirring unit, vacuum adapter, and nitrogen inlet is set up. The kettle is evacuated to a pressure of about 0.5 mm Hg and then purged with nitrogen. The kettle is charged with 9.15 g of paxTMC-1, which is pre-dried by heating it to 220° C. paxTMC-1 is prepared by combining trimethylene carbonate (TMC) and trimethylolpropane (TMP) at a TMC:TMP molar ratio of 15:1, in the presence of a tin catalyst such as stannous octanoate, with heating and stirring. Also added to the kettle is glycolide (313.8 g, 2.705 mol), ε-caprolactone (132.1 g, 1.159 mol) and a radiopacifier. In one embodiment, the radiopacifier is barium sulfate microparticles (245 g, having a diameter between 1 and 4 microns. The apparatus is lowered into an oil bath, and its contents are placed under vacuum at 40° C. for 1 hour, and then the system is purged with nitrogen. The temperature of the oil bath is increased to 95° C. and the kettle contents are mixed thoroughly. After a homogenous fluid composition is attained, a 0.2 M toluene solution of stannous octanoate (2.576 mL, 5.152×10-4 moles stannous octanoate) is added. The temperature of the oil bath is increased to 180° C. whereupon the polymerization reaction takes place and stirring is continued for as long as possible. After stirring is not possible (due to high viscosity), the reaction product is maintained at 180° C. for 7 hours.

The kettle is allowed to cool to room temperature and then lowered into a cold bath to freeze the polymer. The frozen polymer is removed from the kettle and ground up. The ground material is sieved to provide a powder having a desired maximum particle size. The sieved powder is transferred to a 2-liter pear shaped glass flask and placed on a Büchi rotavapor. After obtaining a vacuum of 0.25 mm Hg, the flask is lowered into an oil bath and the temperature is increased to 40° C. After 2 hours at 40° C. the temperature of the oil bath is increased to 80° C., and after 1 hour at 80° C. the temperature is increased to 110° C. The temperature is maintained at 110° C. for 4 hours.

The identity, particle size and amount of the radiopacifier may be selected to provide a desired impact on the implant degradation profile. In general, a sufficient amount of radiopacifier should be included in the composition to allow the composition to be visualized. Extra radiopacifier, i.e., an amount of radiopacifier that is above and beyond the amount needed for visualization, may be included in the composition in order to impact the degradation rate of the composition. While not intending to be bound by theory, it is believed that extra radiopacifier creates stress points within the composition that encourages degradation. If, for example, at least 20 weight percent of radiopacifier should be present in order to visualize the implant, then in various embodiments the present disclosure provides compositions that contain at least 5%, or at least 10% (2 additional weight percent), or at least 15%, or at least 20% (4 additional weight percent), or at least 25%, or at least 30% (6 additional weight percent), or at least 35%, or at least 40% (8 additional weight percent), or at least 45%, or at least 50% (10 additional weight percent), or at least 55%, or at least 60%, or at least 65%, or at least 70%, or at least 75% extra radiopacifier.

In addition to selecting the amount of radiopacifier, one can select the particle size of the radiopacifier. Radiopacifier particles of various sizes and size distributions are commercially available from, e.g., Sigma-Aldrich, St. Louis Mo. The radiopacifier, such as barium sulfate, may have a nominal particle diameter of from about 1.0 to about 20 microns. In embodiments, the radiopacifier used in the medical devices of the present disclosure has a nominal particle size of at least 1.0, or 2.0, or 3.0, or 4.0, or 5.0, or 6.0, or 7.0, or 8.0, or 9.0, or 10.0, or 11.0, or 12.0, or 13.0, or 14.0, or 15.0, or 16.0, or 18.0, or 19.0 or 20.0, each value in units of microns. Optionally, the maximum particle size may be stated at 20.0, or 19.0, or 18.0, or 17.0, or 16.0, or 15.0, or 14.0, or 13.0, or 12.0, or 11.0, or 10.0, or 9.0, or 8.0, or 7.0, or 6.0, or 5.0, or 4.0, or 3.0, or 2.0, or 1.0, again with each value being in units of microns. In general, larger particles impart a faster degradation profile to the medical device, since larger particles impart larger stress concentrations within the resulting fiber, leading to earlier loss in tensile properties and ultimately earlier fragmentation. A higher weight percentage of radiopacifier particle also contributes to a faster degradation profile.

In general, a lower concentration of a higher density radiopacifer may be employed. Barium sulfate has a density of 4.5 g/cm3, and so more barium sulfate must generally be loaded into a medical device in order to achieve effective visualization compared to, e.g., tantalum oxide, tungsten metal and zirconium oxides which are examples of radiopacifier that are denser than barium sulfate. $Bi_2O_2(CO_3)$, i.e., bismuth subcarbonate, BiOCl, i.e., bismuth oxychloride, and $Bi_2O_3$, i.e., bismuth trioxide, in particulate form, are other radiopacifiers that may be incorporated into medical devices of the present disclosure.

In one embodiment, the radiopacifier is present during the polymerization process, while in another embodiment the radiopacifier is added to the pre-formed polymer.

Example 2

Melt-Spinning and Properties of Radiopaque Monofilaments Using MG5-B from Example 1 and its Processing into a Coiled Scaffold (CS)

A single screw extruder with four zones is used to extrude q polymer into monofilament. For example, the polymer from Example 1 is extruded using a 0.6 mm die. A 325 line per inch filter pack is used. Zone 1 is maintained at 100° C., zone 2 is maintained at 175° C., zone 3 is maintained at 212° C., and zone 4/Spin Pack are maintained at 214° C. The metering pump is operated at 8 rpm while the take up roll is set at 40-60 rpm. The collected monofilament may have diameters between 0.58 mm and 0.61 mm. The fiber is drawn at 4.5× in the first stage at 55° C. and 0.5× in the second stage at 70° C., resulting in a diameter of 0.30 mm to 0.33 mm. The free shrinkage is about 8.85% to 10.43% at 50° C. The fiber is relaxed one half the free shrinkage plus 2% at 70° C. The resulting fiber may have a maximum load of about 13N and is dimensionally stable.

The processed radiopaque monofilament is then coiled in a helical manner around a 0.55" diameter Teflon cord which maintains the inner diameter of the coil scaffold. The monofilament is wrapped around the Teflon cord at 33 to 35 coils per inch.

Example 3

Synthesis and Characterization of a Triaxial, Segmented Glycolide Copolymer (MG-9) for Use in Preparing Knitted Scaffolds A reaction apparatus including a 1 L stainless steel kettle with a 3-neck glass lid equipped with an overhead mechanical stirring unit, vacuum adapter, and nitrogen inlet was set up. After obtaining a vacuum of 0.5 mmHg, the apparatus was purged with nitrogen. An initial charge of paxTMC-1 (16.0 g, as described in Example 1), ε-caprolactone (38.6 g, 0.3382 moles), and glycolide (745.4 g, 6.4262 moles) are added to the kettle. The apparatus is then lowered into an oil bath. The kettle and the contents are heated to 110° C. and mixed under positive nitrogen pressure. Once the polymeric initiator appears to be thoroughly dissolved into the monomer, a 0.2 M toluene solution of stannous octanoate (0.966 ml, $1.933 \times 10^{-4}$ moles) is added. The temperature is increased to 180° C. Stirring is stopped when the resulting polymer mixture gets too viscous to stir. The reaction is maintained at 180° C. for 5 hours. The polymer is frozen, removed and ground. The ground material is sieved. Sieved polymer is transferred to a 2 L pear shaped glass flask and placed on a Büchi rotavapor. After obtaining a vacuum of 0.5 mmHg, the flask is lowered into an oil bath. The temperature is increased to 40° C. After 2 hours at 40° C., the temperature of the oil bath is increased to 80° C. After 1 hour at 80° C., the temperature is increased to 110° C. Temperature is maintained at 110° C. for 4 hours.

Example 4

Melt-Spinning and Properties of Multifilament Yarn Using MG-9 from Example 3 and its Processing to a Knitted Scaffold (KS)

A single screw extruder with five zones is used to extrude a polymer into multifilament. The polymer from Example 3 is extruded using a 20 hole die with 0.018" diameter holes. A 400 line per inch filter pack is used. Zone 1 is maintained at 190° C., zone 2 is maintained at 210° C., zone 3 is maintained at 222° C., zone 4/pump are maintained at 228° C., and zone 5/spin pack are maintained at 228° C. A 0.584 cc/rev Zenith metering pump is operated at 6.0 rpm while the denier control roll is set to a linear speed of 315 meters/minute. The fiber is then oriented over three high speed godets traveling at 320, 465, 480 M/minute and heated to 60° C., 80° C., and 26° C., respectively. The collected multifilament is then reoriented at speeds of 250 M/minute to 280 M/minute, and at a temperature of 100° C. The resulting fiber may have a tenacity of 3.26 and a denier of 80.4. The processed multifilament is then plied once to generate a 40 filament fiber and then weft knitted using a lamb circular knitter onto the coiled scaffold from Example 2 in a continuous manner. A ⅞" knitting cylinder with 12 course gauge needles is used to form a knitted scaffold over the coiled scaffold.

Example 5

Synthesis and Characterization of a Triaxial, Segmented l-Lactide Copolymer (SVG-12) for Use as a Reinforced Composite Matrix (CM)

A reaction apparatus including a 4 L stainless steel reactor equipped with an overhead mechanical stirring unit, vacuum adapter, and nitrogen inlet is assembled. After obtaining a vacuum of less than 0.5 mmHg, the apparatus is purged with nitrogen. Oil is heated and circulated through the jacketed reactor to control the temperature. An initial charge of glycolide (254.9 g, 2.1976 moles), trimethylene carbonate (348.7 g, 3.4185 moles), predried triethanolamine (3.0319 g, $2.0348 \times 10^{-2}$ moles), stannous octanoate (354.5 mg, $8.752 \times 10^{-4}$ moles), and ε-caprolactone (974.3 g, 8.5463 moles) is added a 2 L flask and dried under high vacuum for 1.25 hours at 40° C. The flask contents are then added to the 4 L reactor. The system is then purged with nitrogen. The temperature of the oil is increased to 175° C. and the contents mixed thoroughly for 6.5 hours and then the temperature is reduced. Once mixed, the final charge, of glycolide (226.6 g, 1.9534 moles) and l-Lactide (1195.5 g, 8.3021 moles) are added. The temperature of the oil is then increased to 135° C. and maintained for 19 hours.

The resulting polymer is removed and dissolved at a concentration of 4 milliliters per 1 gram in dichloromethane (DCM) so that the polymer can be precipitated out in −60° C. isopropyl alcohol (IPA) and any monomer will stay dissolved and be rinsed away. The polymer is then allowed to dry to a constant weight.

Example 6

Assembling a Composite Ureteral Stent Construct

Preparation of polymer matrix solution—A polymer solution containing SVG-12 from Example 5, polyethylene glycol ($M_W$=4600) and acetone is prepared by addition of 1600 milliliters of acetone to one 64-ounce jar, followed by addition of 16.0 grams of PEG 4600 and 144.0 grams of purified SVG-12. The solution is enclosed and brief heating is used to facilitate dissolution. The jar is placed on automatic rolling apparatus until complete dissolution was reached.

Continuous impregnating of knitted core—The dry, knitted core is impregnated with a polymer matrix of SVG-12 and PEG 4600 using a continuous matrix-impregnating process that involves the continuous movement of the knitted core material through a 0.75-liter bath of polymer solution. The knitted core is unspooled from the beginning of the impregnating apparatus and immediately fed into the bath of polymer solution, where two in-line submerged pulleys keep the scaffold material submerged for the length of the bath. As the impregnated material exits the bath, it is passed through an air-circulating drying tube heated to 40° C., then a stainless-steel element heated to 50° C., and then the impregnated material is spooled onto a final take-up spool.

Shape-forming of impregnated, knitted core—The impregnated material is wrapped onto racks equipped with two parallel stainless steel bars of 0.5 inch diameter, which can be adjusted for separation distance to control final stent length. The newly-impregnated, knitted core is wrapped onto these racks in a continuous fashion. The racks are annealed at 130° C. for 30 minutes, and then the racks are allowed to cool to room temperature in a laminar flow hood. Multiple stents are removed from each rack by cutting the scaffolding material at appropriate positions along interior positions of the separation rods of the shape-forming racks. These stents, which still contained the Teflon core, are modified by addition of a UVJ marker to each stent stem within one centimeter of what would ultimately become the proximal loop of each stent. Then, the proximal loops of all stents are given an additional coating by hand-dipping each proximal loop into 150 milliliters of a 10% (w/v; 9.3% SVG-12, 0.7% PEG 4600) polymer solution of SVG-12 and PEG 4600 in acetone. Stents are hung by distal loops in a laminar flow hood to dry. Then, the Teflon cores are removed from each stent by securing one end of the Teflon core to position-fixed vise-grip pliers as the opposite end of the Teflon core is stretched using a second set of vise-grip pliers. A clean cut is made in the stretched Teflon core at the secured end, and then the Teflon core of reduced diameter is pulled through the stent and discarded. Finally, each stent is trimmed to the appropriate specifications.

Example 7

Assembling a Composite Ureteral Stent Construct

Preparation of polymer solution. A polymer solution was prepared by combining 16.0 grams of polyethylene glycol (PEG 4600; $M_W$=4600), 1600 milliliters of acetone, and 144.0 grams of purified SVG-12 in a jar. The solution is enclosed and brief heating is used to facilitate dissolution. The jar is placed on automatic rolling apparatus until complete dissolution is reached.

The dry, knitted scaffold from Example 4 is impregnated with the polymer solution described above using a continuous impregnating process that involved the continuous movement of the knitted core material through a 0.75-liter bath of polymer solution. The scaffold is unspooled and fed into a bath of coating solution, where two in-line submerged pulleys keep the scaffold material submerged for the length of the bath. As the impregnated material exits the bath, it passes through an air-circulating drying tube heated to 40° C., then a stainless-steel element heated to 50° C., and then the impregnated material is spooling onto a final take-up spool. This process is repeated in order to provide a thicker coating on the scaffold, where the thicker coating has a smooth surface.

The impregnated knitted scaffold is wrapped onto racks equipped with two parallel stainless steel bars of 0.5 inch diameter, which can be adjusted for separation distance to control final stent length. The newly-impregnated, knitted scaffold is wrapped onto these racks in a continuous fashion. The racks are annealed at 130° C. for 30 minutes, and then the racks are allowed to cool to room temperature in a laminar flow hood.

Multiple stents are removed from each rack by cutting the scaffolding material at appropriate positions along interior positions of the separation rods of the shape-forming racks. These stents, which still contain the Teflon core, are modified by addition of a UVJ marker to each stent stem within one centimeter of what would ultimately become the proximal loop of each stent.

The proximal loops of the stents are given an additional coating by using an MTS Synergie testing apparatus to mechanically dip the proximal end of the stent into a coating solution in a controlled manner and using multiple cycles. The distal end of the stent is attached to the vertical fixture on the MTS testing apparatus, which is programmed to dip the stent into a 100 mL graduated cylinder containing 100 mL of the coating solution. The programmed procedure lowers the stent into the cylinder to the 20 mL marking and immediately raises the stent out of the cylinder. The MTS apparatus pauses for a time sufficient to dry the coating until it reaches a non-tacky state, about 30-300 seconds as the stent is suspended above the coating solution, and then the dipping procedure is repeated, with the exception that the stent is lowered to the 40 mL marking. The MTS program performs two final dipping cycles, wherein the stent is lowered to the 60 mL and then to 80 mL mark. This results in an exterior coating layer that has a thickness gradient, wherein the thickest layer of coating is located on the proximal loop. This ensures that the proximal loop is reinforced with more coating material than the rest of the stent so that the proximal loop does not degrade prematurely.

Stents are hung by distal loops in a laminar flow hood to dry. Then, TEFLON™ PTFE cores are removed from each stent by securing one end of the TEFLON core to position-fixed vise-grip pliers as the opposite end of the TEFLON is stretched using a second set of vise-grip pliers. A clean cut is made in the stretched TEFLON core at the secured end, and then the Teflon core of reduced diameter is pulled through the stent and discarded. Finally, each stent is trimmed to the appropriate specifications.

The resulting stents have a fast-degrading internal structure (knitted scaffold) and a hydrophilic, exterior containment layer that degrades more slowly than the internal structure. The internal structure degrades and is completely eliminated within 4 days, or 1 week, or 2-4 weeks, or within 2-7 weeks, or as long as 90 days, or as long as six months, whereas the longer lasting containment layer is still present after the internal structure is completely degraded, such that the containment layer is present for at least 4 weeks before it is degraded and excreted. As a result, the containment layer functions to retain the internal structure and its degradation products until complete degradation and excretion occurs. This function of the containment layer prevents degradation products of fast-degrading material from entering the kidney which can result in complications requiring removal of remnant material that can cause blockage etc. This is an example of a containment layer that may be used in connection with a medical device, e.g., any of the medical devices disclosed herein, to provide managed degradation when the device is implanted into a host.

Example 8

Containment Layer that May be Used in Connection with a Medical Device to Provide Managed Degradation This example provides a bioabsorbable ureteral stent comprising an inner containment layer, an intermediate monofilament coil in a helical configuration, a weft-knit mesh on the exterior of the monofilament coil, and an exterior, hydrophilic containment layer applied as an outer layer that also penetrates and fills voids and empty spaces between material of the other three components—particularly the intermediate coil and weft-knit mesh components. The exterior containment layer degrades more slowly than the monofilament coil and the weft-knit mesh components, resulting in a containment layer that functions to retain degradation products of the coil and mesh that degrade within 2-4 weeks.

The first step in constructing the multi-component bioabsorbable ureteral stent involves applying an inner coating layer to a monofilament cord of polytetrafluoroethylene (PTFE) having a diameter of approximately 0.055 inches. The inner coating layer will function as the inner containment layer. The PTFE monofilament cord is coated according to the drawing process disclosed in Example 1, however PTFE monofilament cord is substituted for the knitted core, a polymer solution of 15% (weight per volume) polymer in acetone is used and the monofilament is coated two times using the procedure described. The monofilament is fed through the polymer solution at a rate not exceeding 6 meters per second (m/s) to ensure that a sufficient thickness of polymeric coating is applied to the surface of the PTFE that the coating can function as a containment layer. This is an example of a containment layer that may be used in connection with a medical device, e.g., any of the medical devices disclosed herein, to provide managed degradation when the device is implanted into a host.

Example 9

Caps that May be Used in Connection with a Medical Device to Manage Degradation

A cap may be added to a stent, where the cap provides some or all of a containment layer. The cap is located at either end of the stent, and bridges across the open lumen of the stent, so as to enclose the capped end of the stent.

A cap may be placed on the stent as exemplified herein. The cap is formed after the removal of the TEFLON monofilament cord from the stent. After the cord has been removed, an end of the stent is dipped into a solution of degradable polymer. This solution is sufficiently viscous such that, after the stent has been removed from the solution, some amount of solution will bridge across the open lumen at the end of the stent, and upon solvent removal through evaporation, will leave a polymer film that covers the dipped end of the stent. This polymer film is the cap. This process may be repeated several times as needed in order to build up a desired thickness for this cap.

As an alternative, a cap may be prepared from a degradable mesh, and the mesh is adhered to the end of the stent so as to form the cap. In this embodiment, the cap is porous, such as is desirable when the stent is a urethral stent. However, the cap need not be porous, or it may only become porous after it has been implanted.

These are examples of caps that may be used in connection with a medical device, e.g., any of the medical devices disclosed herein, to provide managed degradation when the device is implanted into a host.

Example 10

Longitudinal Slitting of Coil Component to Create a Predictable Failure Point in the Coil Component Glycolide copolymer (MG5-B) is prepared into a stabilized monofilament through melt extrusion and oriented to create a fiber with diameter of about 0.3 mm, which is further processed through a coiling process onto a 0.055" diameter Teflon cord to maintain the inner diameter of the coil. After coiling and while still on the Teflon cord, the coil component passes along a fixed knife edge cutter to impart a longitudinal slit of approximately 0.02 mm in depth transverse to the fiber axis and axially along the coil length.

The longitudinal slit reduces the initial tensile strength by a small amount, e.g., about 5%. The tensile strength is measured by upwrapping the monofilament from the cord and then placing a segment of monofilament into a tensile strength tester. As a consequence of the cutting, there is obtained a coiled, slitted scaffold having 33 to 35 coils per inch of glycolide copolymer monofilament and a transverse slit along the length of the scaffold. In vivo, the implant will fracture along the slit points, and degradation will occur initially at the locations of the slit.

The depth of the slit may be selected in view of the diameter of the monofilament. In various embodiments, the depth of the slit may be 1% or 2% or 3% or 4% or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35% of the diameter of the monofilament, including ranges selected from these percentage values.

This is an example of a slit that may be created in a medical device, e.g., any of the medical devices disclosed herein, to provide managed degradation when the device is implanted into a host.

Example 11

Preparation of a Degradable Ureteral Stent Containing a Longitudinal Defect to Provide Predictable Degradation Failure Points Glycoprene polymer (prepared from 93% glycolide, 5% caprolactone, and 3% trimethylene carbonate) formed into a multifilament fiber and having a tenacity of 3.26 and 4.0 denier per filament is prepared through a melt extrusion process. A Lamb circular weft knitter is used to form a knit of Glycoprene multifilament fiber over the coiled and slitted scaffold from Example 10 in a continuous manner. A ⅞" knitting cylinder with 12 course gauge needles is used to form the knitted scaffold over the coiled and slitted scaffold.

In a separate container, a polymer solution containing SVG-12, polyethylene glycol ($M_w$=4600) and acetone is prepared by addition of 1600 mL of acetone to one 64-oz jar followed by addition of 16.0 grams of PEG 4600 and 144 grams of SVG-12. The solution is enclosed and briefly heated to facilitate dissolution. The jar is placed on an automatic rolling apparatus until complete dissolution is reached. Continuous impregnation of the knitted core [everything goes through this bath; even the Teflon core] is performed by the continuous movement of a knitted core through a 0.75-liter bath of polymer solution. The knitted core is unspooled from the beginning of the impregnating apparatus (consisting of the spools; the coating bath; and the collection spool) and immediately fed into the bath of polymer solution, where two in-line submerged pulleys keep the scaffold materials submerged for the length of the bath. As the impregnated material exits the bath, it is passed through an air-circulating drying tube heated to 40° C., then a stainless steel element heated to 50° C., and then collected onto a final take-up spool, where it is stored under reduced pressure to complete the drying process.

Stents are formed from the impregnated, knitted core by wrapping onto racks equipped with two parallel stainless steel bars of 0.5 inch diameter, which are adjustable for separation distance to control final stent length. Once placed on the forming rack, the structure is annealed at 130° C. for 30 minutes and allowed to cool to room temperature in a laminar flow hood. The stents are cut from the forming rack into the final net shape of the Degradable Ureteral Stent and the Teflon core removed by securing one end of the Teflon to position-fixed vice grip as the opposite end is used to stretch the Teflon core to reduce diameter allowing removal from the stent length. Each stent created in this way is inspected to the appropriate specification.

Through this technique of coating and shape forming, the longitudinal slit created along the length of the inner coil remains but is initially protected due to the impregnation process. This is an example of a slitting and coating technique that may be used in connection with a medical device, e.g., any of the medical devices disclosed herein, to provide managed degradation when the device is implanted into a host.

Example 12

In Vitro Hydrolysis of Stent Prepared with a Longitudinal Slitting of the Coil Component The impregnated and shaped degradable ureteral stent from Example 11 degrades primarily from hydrolysis of main chain esters of the polymer backbone. As the stent reaches late stage degradation, there is potential of the MG5-B monofilament coil component to define the length of fragment generated, whereas longer fragment lengths may have elevated potential to partially or fully obstruct the ureteral sphincters, leading to temporary incontinence. During in vitro hydrolysis of the impregnated and shaped degradable ureteral stent from Example 11, the longitudinal slit creates a defect that is predisposed to fracture at the slit site. Upon incubation in artificial urine at 37° C., the degradable stent initially loses strength along the entire length of the stent while maintaining bulk form for the first about 5-7 days (compared to about 7-12 days if the slit is absent). See ASTM F1828-97 (Reapproved 2006), preparation method A1.2 for the composition of the artificial urine.

After this time, degradation primarily within the MG5-B monofilament coil has reduced the tensile strength, approximately to less than about 20% of the initial strength, creating a friable monofilament that can fracture with mechanical input. The coil initially fractures at the slit location prior to fragmenting from the degradable ureteral stent. This fragment is of between 0.03 mm to 15 mm in length, which then readily fractures into smaller segment lengths with stent movement. The degradable ureteral stent as described in Example 11 hydrolyses into segment lengths suitable for passage from the urinogenital conduit within about 30 days of placement.

Example 13

Alternative Mechanisms for Creating a Defect to Provide a Predictable Coil Failure Point A defect that creates managed degradation of a biodegradable medical implant may be imparted in a number of ways. As previously exemplified, the coiled form of monofilament may be cut to provide a slit of a specified depth. The cut depth may be selected to have a desired impact on the fiber tensile strength, with increasing depth of cut directly correlated with increasing loss in tensile strength. Cut depths of more than 30% of the fiber diameter may result in a tensile strength loss of 50% or more from the initial strength, yielding mechanical performance of the coil which may be below that needed to maintain ureter patency. Accordingly, in one embodiment the cut depth is less than 30% of the diameter of the coiled monofilament. Increased cut depth provides faster degradation of the coil portion of the stent, however this must be balanced against providing the strength retention time required for stent functionality.

The cut need not be uniform. For example, shallow cuts of at least 0.03 mm may be made in an interrupted manner along the axis of the coil as opposed to a continuous manner in which each individual coil has a cut. This may serve to create larger fragments of the stent during the degradation process, whereas stent fragments that are longer than 10 mm may not be desirable due to the potential for obstruction.

Instead of creating a cut along the coil with a knife-edge cutter, alternative techniques to disrupt the coil portion of the medical device may be employed. For example, a laser may be used to create a slit by ablating between 3-30% of the coil diameter from the stent without creating a large heat affected zone.

The laser may also, or alternatively, be used to provide a point energy source to create one or more regions of stress through disorganizing the polymer crystalline structure, imparting stresses within the coil polymer, and degrading the polymer chain length, all in order to elicit a more rapid degradation. A combination of heating and laser ablation may also be used for a combined effect.

These are examples of creating defects in a medical device, e.g., any of the medical devices disclosed herein, to provide managed degradation when the device is implanted into a host.

Example 14

Creation of a Degradation Site Through the Selective Removal of Stent Impregnation Coating An impregnated and shaped degradable ureteral stent may be modified to encourage degradation into smaller sections through the selective removal of the impregnation coating along the length of the stent. The impregnated and formed stent may be processed by removing circumferential bands of coating spaced a distance part, e.g., 1 cm apart, along the shaft length, i.e., along the mid-section of the stent. This may be accomplished by applying a suitable solvent such as acetone to dissolve the impregnation coating in a narrow band of a desired width, for example, of approximately 1 mm in width, from the shaft, and around the entire circumference of the stent. This process exposes the treated sections of knit and coil components of the stent. The resulting stent comprises a continuous coil, e.g., formed of MG5-B, a continuous knitted component encasing the coil, and an impregnation coating along the length of the stent in sections of, e.g., 1 cm in length followed by spacing, e.g., a 1 mm separation, prior to the next section of impregnated coating.

This illustrates how to create a defect in a medical device which may be applied to any medical device, including any of the medical devices disclosed herein, to provide managed degradation when the device is implanted into a host.

Example 15

In Vitro Hydrolysis of the Degradable Ureteral Stent with Selectively Removed Sections of Impregnation Coating The impregnation coating of a stent acts essentially as a passivation layer to control the rate of hydrolysis of the underlying coil component as well as the knitted component. During hydrolysis of the stent created in Example 14, sections with coating removed are less protected from degradation. In vitro hydrolysis of the stent from Example 14 may be performed using simulated urine at 37° C. Sections of the stent with the impregnation coating selectively removed are expected to lose strength approximately 20% faster than those with coating, encouraging fractures to occur at those sites thereby generating degraded lengths of approximately 1 cm to allow easier clearance from the ureter and bladder without obstruction.

Example 16

Method of Creating a Preferred Degradation Vector Through the Application of Ionizing Radiation The application of ionizing radiation may be used to reduce the molecular weight of synthetic bioresorbable polyesters. In an effort to generate a preferred degradation vector or gradient in a stent, beta radiation may be applied from one direction along the length of the stent with a total exposure of the bladder curl side of the stent of about 10-50 kGy, transitioning to about a 50% reduced irradiation dose at the kidney curl side of the stent.

To generate this dose vector, the stent as described in Example 6 is placed in a metal foil pouch and dried under reduced pressure at room temperature to minimize residual moisture. The packaged is then hermetically sealed in a nitrogen atmosphere to provide protection from light and moisture. The sealed packages containing the stent are packaged with the bladder curl end upright in a single layer for processing.

Electron irradiation, a process involving beta radiation of high energy is applied to the packaged stent. In this technique, a cathode source is used to generate electrons that are accelerated and shaped into a collimated beam. This process produces radiation which is limited in the depth of penetration. By applying this technique to a box containing stents where the stents are oriented such that the bladder curl is closest to the radiation source, the bladder curl receives an elevated dose of radiation, with effective applied dosage lessening through the length of the packaging, ultimately with the kidney curl end of the stent obtaining approximately 60% of the radiation energy of the bladder curl end.

By creating a stent with progressive radiation dose, the degradation profile is modulated such that the stent preferentially fractures starting at the bladder curl progressing towards the kidney curl, thereby promoting small size degradation products which minimize risk of stent-induced incontinence.

The present disclosure thus provides a process for producing a medical device wherein electron radiation is applied in a non-uniform manner across the device, so that the device itself comprises a polymer having a non-uniform molecular weight ($M_w$ or $M_n$) across the device. The present disclosure also provides devices that have a gradually changing non-uninform polymer molecular weight ($M_w$ or $M_n$) across a dimension of the device.

This illustrates how to create a defect in a specific medical device where this approach may be applied to any medical device, including any of the medical devices disclosed herein, to provide managed degradation when the device is implanted into a host.

Example 17

Method of Creating a Preferred Degradation Vector Through the Modulation of Coil Pattern & Coil Density A primary mechanism for shape retention during degradation is the presence of the MG5-B coil within a stent. In order to create a preferential degradation path, in one embodiment the stent coil is modulated along the length of the stent shaft during coil manufacturing. To achieve this result, a Teflon monofilament acts as a core to create and maintain the inner lumen of the stent during manufacturing. MG5-B or other monofilament fiber is wrapped around the Teflon core to create the coil component of the stent. During coil creation, sections of the coil that will ultimately become the bladder curl and kidney curl are formed at a coil density of about 33 to 35 coils per inch. In the shaft region of the stent, which forms the mid-section of the stent, the coil is created with a modulated coil density progressing from about 33 to 35 coils per inch at the kidney curl transition to about 15 to 20 coils per inch at the bladder curl transition.

These coil densities may be varied at the beginning, the end, and along the shaft. For example, the shaft region of the stent may have a coil density at one of the shaft (e.g., near the kidney curl transition) of, for example 30, or 31, or 32, or 33, or 35 coils/inch. The coil density may gradually decrease along the length of the shaft. For example, at the bladder coil transition the coil density may only be, for example, 12, or 13, or 14, or 15, or 16, or 17, or 18, or 19, or 20, or 21, or 22, or 23, or 24, or 25 coils/inch.

During in vitro degradation at 37° C. in simulated urine, the section of the stent shaft with 15-20 coils per inch loses strength to a level that supports stent fracture several days, e.g., 1, or 2, or 3 or 4 or 5 days earlier than the transition closest to the kidney, providing a bladder-to-kidney degradation vector. As the stent shaft progressively begins to fracture, small sections are separated from the stent shaft providing a "bottom-up" degradation path and minimizing the risk of stent-induced incontinence.

This illustrates how to create a degradation vector in a specific medical device where this approach may be applied to any medical device, including any of the medical devices disclosed herein, to provide managed degradation when the device is implanted into a host.

Example 18

Alternative Methods of Creating a Preferred Degradation Vector Through the Modulation of Stent Components In additional embodiments, alternative techniques may be used in order to create a preferred degradation vector along the stent shaft.

The impregnation coating may be applied to a coil, e.g., an MG5-B-based coil, on a Teflon core through a spray coating technique, where the deposited thickness is varied along the length of the shaft. According to this approach, the impregnation coating thickness is applied at a level of 8 wt % of the total weight of MG5-B+Glycoprene+SVG12/PEG on both curls as well as at the kidney curl transition, while the coating is applied at a level of 4 wt % at the bladder curl transition, with a linear coating gradient between the bladder and kidney curl. By this approach, the integrity of the stent is lost first at the bladder end of the shaft.

In other embodiments, the impregnation coating thickness is applied at a level of 5 wt %, or 6 wt %, or 7 wt %, or 8 wt %, or 9 wt %, or 10 wt %, or 11 wt %, or 12 wt % of the total weight of MG5-B+Glycoprene+SVG12/PEG on both curls as well as at the kidney curl transition, while the coating is applied at a lower level at the bladder curl transition, with a linear coating gradient between the bladder and kidney curl. For example, if the impregnation coating thickness is at a maximum of 12 wt %, the coating thickness may gradually decrease to 11 wt %, then 10 wt %, then 9 wt %, then 8 wt %, etc. down to the desired thickness, thus creating a coating thickness gradient.

These examples illustrate how to create a degradation vector in a specific medical device where these approaches may be applied to any medical device, including any of the medical devices disclosed herein, to provide managed degradation when the device is implanted into a host.

Example 19

Alternative Methods of Creating a Preferred Degradation Vector Through the Modulation of Stent Components Another way to create a preferred degradation vector for a stent having a coil, knit, and coating construct as described earlier is to plasma treat the surface of the device. Plasma treatment will add hydroxyl groups to the surface of the device, which will recruit more water when the device is implant in a host, and thereby encourage degradation at the surface. The plasma treatment may be selective so that some surfaces receive more plasma treatment, and accordingly have more hydroxyl groups, than other surfaces. In this way, a gradient of hydroxyl groups be created along the stent shaft with the highest level of exposure at the bladder curl transition to increase local hydrophilicity and locally degrade/disorganize the polymers, thereby encouraging initial strength loss to occur closest to the bladder curl, progressing along the stent shaft towards the kidney curl.

This chemical treatment to induce early degradation may be applied through alternative means as well, including acid treatment at varying levels to induce chain scission and hydrophilicity. Additionally, the spray coating composition may be modulated along the length of the stent by changing the ratio of PEG 4,600 to SVG12, with a higher concentration of PEG 4,600 at the bladder curl transition and lower concentration at the kidney curl transition.

This illustrates how to create a degradation vector in a specific medical device where this approach may be applied to any medical device, including any of the medical devices disclosed herein, to provide managed degradation when the device is implanted into a host. Thus, the present disclosure provides a method of forming a stent, the method comprising constructing a stent from components comprising a coil, a knit, and a coating, and then subjecting the stent to chemical treatment to induce early degradation of the stent when it is implanted into a host.

Example 20

Design and Manufacturing to Create Layered Core-to-Sheath Degradation Vector

A degradable ureter stent having an innermost coil made from a radiopaque, glycolide-based monofilament, overknit with a glycolide-based multifilament, and subsequently sheathed with a degradable polymeric film, where the monofilament coil exhibits the fastest degradation profile, followed shortly by the overknit multilament, and lastly the film sheath exhibiting the longest degradation life.

MG5-B monofilament coil of 0.3 mm diameter is wound onto a Teflon core having a 0.055" diameter at between 33 and 35 coils per inch. A Lamb circular weft knitter is used to form a knit of Glycoprene multifilament fiber over the coiled and slitted scaffold described previously in a continuous manner. A ⅞" knitting cylinder with 12 course gauge needles is used to form the knitted scaffold over the coiled scaffold. A ¾" single barrel custom melt extruder with a tubing die heated to approximately 165° C. is used to extrude SVG-12 and polyethylene glycol blend into a thin sheath. The coiled and knitted Teflon assembly is passed through the tubing die head allowing direct application of the thin tubular sheath.

Stents are formed from the impregnated, knitted core by wrapping onto racks equipped with two parallel stainless steel bars of 0.5 inch diameter, which are adjustable for separation distance to control final stent length. Once placed on the forming rack, the structure is annealed at 130° C. for 30 minutes and allowed to cool to room temperature in a laminar flow hood. The stents are cut from the forming rack into the final net shape of the degradable ureter stent and the Teflon core removed by securing one end of the Teflon to position-fixed vice grip as the opposite end is used to stretch the Teflon core to reduce diameter allowing removal from the stent length. Each stent created in this way is inspected to the appropriate specification. In this manner, a degradable ureter stent may be prepared such that the SVG-12 and PEG sheath remain as a distinct layer which maintains the stent outer diameter but does not individually coat the MG5-B coil or Glycoprene knit.

During in vitro degradation at 37° C. in simulated urine, the MG5-B coil loses strength at between about 7 and 14 days, after which it fragments and is easily displaced from the remaining Glycoprene fiber and outer sheath. As the coil, and later the knit, fragment they may separate from the residual stent and settle in the bladder, further degrading to smaller fragments before excretion with simulated urination. Likewise, the SVG-12/PEG sheath may collect in the bladder and fragments before excretion with simulated urination.

This illustrates how to create a degradation vector in a specific component of a medical device where this approach may be applied to any medical device, including any of the medical devices disclosed herein, to provide managed degradation when the device is implanted into a host.

Example 21

Multiple Coil Inclusion to Control Rate of Coil Separation

Polydioxanone polymer is melt-extruded using a ¾" single screw extruder into a monofilament, followed by orientation and heat treatment to create a thermally stable, strong monofilament with 0.3 mm diameter. MG5-B stabilized monofilament fiber is coiled onto a monofilament Teflon core with 0.055" diameter in a continuous manner using a Lamb circular knitter. In alternating sections of 15 cm, the polydioxanone monofilament is co-coiled with the MG5-B monofilament to impart a second coil component. Throughout both sections of coil (with and without polydioxanone monofilament), the net coil density remains constant at between 33 and 35 coils per inch. The resulting coil is processed into a finished degradable ureter stent as described in Example 6 to form a stent with MG5-B-only coil from roughly the midpoint of the shaft through the bladder curl. The portion of the stent between the shaft midpoint and the tip of the kidney curl contains coil of both MG5-B and polydioxanone monofilaments.

During in vitro degradation at 37° C. in simulated urine, the section of the stent below the midpoint of the shaft will fracture and separate from the stent body first. The MG5-B coil within the kidney half of the stent will be retained within the stent due to the extended strength retention of the second coil component. After 14 days, when the MG5-B is significantly degraded and fragmented, the polydioxanone coil begins to fragment, releasing fine particulate MG5-B, the residual coating and knit components, ultimately allowing the residual polydioxanone coil to transfer into the bladder. These fragments are further degraded within the bladder until excreted through simulated urination.

Thus, the present disclosure provides medical devices comprising two different polymers, each having a unique degradation profile (i.e., the two polymers have different degradation profiles, one from another), where the two polymers are each used to prepare the same component of the medical device. In this example, that same component is the coil of a stent. Thus, the coil component of the stent is made from two coils, where the two coils comprise different polymers having different degradation profiles.

Example 22

Manufacturing Alternatives to Generate Discrete Degradation Particulate:
Modulated Monofilament Diameter The coil component of a degradable ureter stent is typically the primary feature for providing structural support for the stent, as well as the primary strength mechanism for maintaining lumen patency once implanted. To encourage the monofilament to degrade into discrete particulates, the coil material, e.g., MG5-B, is melt-extruded into a continuous monofilament and oriented with between 2× and 5.5× draw ratio in a pulsatile manner with a period of 5 mm so that the resulting fiber exhibits a diameter of 0.3 mm at the crest and 0.2 mm at the trough. These diameter values are exemplary only: other non-identical diameter values may also be created using the pulsatile manner of extrusion. This monofilament is subsequently processed by wrapping onto a Teflon core having 0.055" diameter at a coil density of between 33 and 35 coils per inch. This coil is additionally processed as described in Example 6 to form a degradable ureter stent.

During in vitro degradation at 37° C. in simulated urine, the MG5-B monofilament with variable diameter preferentially degrades at the smallest diameter sections of the monofilament, generating MG5-B particulates which are approximately 5 mm in length.

This illustrates how to create a non-homogeneity in a specific medical device where this approach may be applied to any medical device having a filament, including any of the medical devices disclosed herein that include a filament, to provide managed degradation when the device is implanted into a host.

Example 23

Manufacturing Alternatives to Generate Discrete Degradation Particulate:
Embossed Monofilament MG5-B monofilament is melt-extruded and oriented into a uniform diameter. In a secondary process, the monofilament is passed through a rotary embosser with a dimple pattern at 2-10 mm increments to generate stress concentration and physical defects along the length of the fiber. Embossed monofilament is then wrapped onto a Teflon core having 0.055" diameter at a coil density of between 33 and 35 coils per inch and further processed as described in Example 6 to form a degradable ureter stent.

During in vitro degradation at 37° C. in simulated urine, the embossed monofilament preferentially degrades at the location of the embossed dimple, generating MG5-B particulates which are approximately 5 mm in length.

This illustrates how to create a defect in a specific medical device where this approach may be applied to any medical device, including any of the medical devices disclosed herein, to provide managed degradation when the device is implanted into a host.

Example 24

Manufacturing Alternatives to Generate Discrete Degradation Particulate:
Heat Treatment MG5-B monofilament is melt-extruded and oriented into a uniform diameter. In a secondary process, the monofilament is partially thermally treated in 2 mm segments along the fiber axis, reducing the crystalline orientation of the MG5-B monofilament. Partially heat treated monofilament is then wrapped onto a Teflon core having 0.055" diameter at a coil density of between 33 and 35 coils per inch and further processed as described in Example 6 to form a degradable ureter stent.

During in vitro degradation at 37° C. in simulated urine, the partially heat treated monofilament preferentially degrades at the location of thermal treatment, generating MG5-B particulate which is approximately 2 mm in length.

This illustrates how to create a defect in a specific medical device where this approach may be applied to any medical device, including any of the medical devices disclosed herein, to provide managed degradation when the device is implanted into a host.

Example 25

Manufacturing Alternatives to Generate Discrete Degradation Particulate:
Ringed Support MG5-B polymer is injection molded into an open ring structure (clip) having an inner lumen diameter of 0.050" and a wall thickness of 0.3 mm. The coil is further designed such that the "top" and "bottom" surface of the clip have flat features for improved stacking and handling during downstream processing and to aid in buckling resistance during stent insertion. These clips are placed on a Teflon core with 0.055" diameter at a spacing of between 30 and 35 clips per inch and remain in place by frictional forces. The Teflon core with MG5-B clips are further processed as described in Example 6 to form a degradable ureter stent.

During in vitro degradation at 37° C. in simulated urine, the injection molded clips separate due to degradation in the knit and coating layers, generating discrete particulates which are less than 0.3 mm in thickness.

This illustrates how to create a defect in a specific medical device where this approach may be applied to any medical device, including any of the medical devices disclosed herein, to provide managed degradation when the device is implanted into a host.

Example 26

Manufacturing Alternatives to Generate Discrete Degradation Particulate:
Islands in the Sea MG5-B and 85:15 PLGA are coextruded into an islands-in-the-sea monofilament configuration, with between 1 and 10 filaments of 85:15 PLGA at 5 denier per filament comprising the "islands" within a "sea" of MG5-B. The monofilament is oriented to increase tensile strength and heat stabilized to optimize thermal stability. This attenuated monofilament is wound around a Teflon core having a 0.055" diameter at a spacing of between 33-35 coils per inch. The coiled Teflon core is further processed as described in Example 6 to form a degradable ureter stent.

During in vitro degradation at 37° C. in simulated urine, the MG5-B component of the coil loses strength before the 85:15 PLGA "islands", which assists in retaining the initial coil structure of the stent until the MG5-B component is degraded such that it fragments into pieces smaller than 0.5 mm. Once the MG5-B component of the coil is separated from the "islands," the filaments generally coalesce into a small, loosely condensed structure allowing easy excretion from the bladder with urination.

This illustrates how to create a defect in a specific medical device where this approach may be applied to any medical device, including any of the medical devices disclosed herein, to provide managed degradation when the device is implanted into a host.

Example 27

Manufacturing Alternatives to Generate Discrete Degradation Particulate:
Monofilament Shape MG5-B polymer is melt extruded using a single screw ¾" extruder with a multi-lobed die having a plurality of fins from a central hub, to create a profile monofilament with a cross sectional area of approximately 0.07 mm². After orientation and heat treatment, the monofilament is coiled around a 0.055" Teflon core at a density of between 33 and 35 coils per inch to form a stent coil.

This illustrates how to create an asymmetric component in a specific medical device where this approach may be applied to any medical device, including any of the medical devices disclosed herein, to provide managed degradation when the device is implanted into a host.

Example 28

Alternative Monofilament Shapes

MG5-B polymer may be melt extruded into a variety of non-circular cross-sectional shapes to control degradation morphology. For example, the polymer may be melt extruded into the form of a bi-lobed monofilament with a narrow central section to induce degradation primarily into two separate longitudinal lengths to increase compliance of the degradation byproduct. Alternatively, the polymer may be melt extruded into the form of a flattened monofilament or a tube to maintain bending stiffness and to maintain stent mechanics while encouraging the degradation of the coil component into smaller particulates.

This illustrates how to create an asymmetric component in a specific medical device where this approach may be applied to any medical device, including any of the medical devices disclosed herein, to provide managed degradation when the device is implanted into a host.

Example 29

Inclusion of Buffering Agent to Counteract Degradation Byproduct Acidity

Degradable ureter stents are prepared as described in Example 6, with a modified coating solution. The coating solution is prepared using SVG-12, polyethylene glycol (Mw=4,600), and micronized dibasic sodium phosphate (e.g., at 5 wt %), dissolved and dispersed into acetone. The resulting degradable ureter stent impregnation coating contains approximately 0.5-3 wt % of dibasic sodium phosphate. After implantation, the dibasic sodium phosphate is released from the coating and assists to buffer the urine against the effects of acidic degradation byproducts to maintain a typical pH level within the urine of between 6.5 and 8.0.

Example 30

Inclusion of Antispasmodic to Counteract Irritation Induced by Foreign Object

Degradable ureter stents are prepared as described in Example 6, with a modified coating solution. The coating solution is prepared using SVG-12, polyethylene glycol (Mw=4,600), and an antispasmodic agent such as Atropine, dissolved and dispersed into acetone. The resulting degradable ureter stent impregnation coating contains at least 0.5 mg of Atropine. After implantation, the Atropine is released from the impregnation coating and acts with anticholinergic action to control spasms within the ureter and urethra which may be caused by the presence of a foreign body or breakdown product therefrom.

Example 31

Stent Surface Feature to Improve Placement Stability

A degradable ureter stent is prepared as described in Example 6 but using a barbed monofilament fiber with 0.3 mm diameter as the coil component. The resulting stent exhibits barbed surface features which act to penetrate into the tissue after placement to reduce the risk of stent migration. Optionally, the stent is produced without a bladder curl as placement location stability is maintained by the presence of the barbs on the stent surface. Optionally, the bladder curl is replaced with a flared section to prevent upward migration of the stent into the kidney.

Example 32

Additive Manufacturing Approach to Form a Degradable Ureter Stent

To create a continually variable degradation path with includes surface features for placement stability, an additive manufacturing approach is utilized. A Stratasys J750 polyjet printer is utilized to deposit three distinct materials to provide component elements of the final stent structure, as described:

Component 1 is a fast-degrading glycolide-based photocurable resin loaded with an inorganic radiopacifier, and is used as a radial stiffening element and printed within the body of the stent as a coil.

Component 2 is a fast-degrading poly(propylene fumarate) photocurable resin which is included axially throughout the shaft of the stent to act as a reinforcing element for placement and potential retrieval.

Component 3 is a flexible trimethylene carbonate-based photocurable resin and is included as a tissue-interfacing covering to form the sheath of the stent and bind components 1 and 2, and also to maintain the net stent shape.

Component 1 is included within the stent such that the orientation and shape of the coil structure provides a flat inner lumen, as well as an outer surface that is textured to increase friction between the ureter wall and the stent surface for improved placement stability.

By modulation of Component 3 thickness within the stent it is possible to provide for faster degradation in specific locations to create defects that fracture at between 1 and 3 days faster than those with more Component 3 covering. Additionally, Component 3 is designed to optionally create a porous (non-continuous) film barrier.

Component 2 is included to maintain continuity of the stent, and is included as an axial component in an interrupted manner to allow for fracture and separation of the stent fragments at specific sites.

The net stent shape, including both bladder curl and kidney curl, are generated in a single process with no need for additional curing or heat treatment. The stent is cleaned in an isopropanol bath at 37° C. for 1 hour to remove residual photoinitiator and unreacted reagents before drying, packaging and sterilization.

During in vitro degradation at 37° C. in simulated urine, fragmentation preferentially occurs in regions with less Component 3. The connectivity of the stent is maintained by Component 2, whereas when the coil fractures stent unity is maintained within the stent structure until coil fracture occurs at an interruption in Component 2. This fracture allows a small section of the stent to break away into the bladder, where it may be excreted with urination.

Example 33

Coil Component Modulus

USD polymer is prepared by ring-opening polymerization with polydioxanone and a PEG macromonomer (Mw=10,000) to form a semi-crystalline polymer having melting temperature of between 100-120° C. The USD polymer is isolated, ground, and sieved to obtain a granule size of between 1-4 mm, and devolitalized to remove residual monomer.

USD polymer is melt-extruded utilizing a ¾" single screw extruder into a monofilament. The monofilament is oriented at between 2× and 5.5× and annealed at 80° C. to increase thermal stability. Fiber tensile testing identifies a tensile modulus of between about 500-800 MPa, which is approximately 2 times that of MG5-B monofilament. USD monofilament is coiled around a Teflon core of 0.055" with a coil density of 30-40 coils/inch, or a coil density between 33 and 35 coils per inch. The coiled monofilament is processed into a degradable ureter stent in the same manner as described in Example 6.

During in vitro degradation at 37° C. in simulated urine, the polyether component of the USD monofilament coil leads to degradation and fragmentation of the coil between about 10 and 21 days, allowing the residual stent fragments to transfer into the bladder. Due to the increased modulus of the USD monofilament compared to MG5-B monofilament, the coil fragments tend to retain the coiled shape and prevent other stent components from collapsing and collating into a dense mass, which may help reduce the risk of incontinence and/or blockage within the urethra.

Example 34

Inherently Radiopaque Polymer

A coating polymer, RS-1, is synthesized using 33% ε-caprolactone, 32% l-lactide, 17% glycolide, 14% trimethylene carbonate, with 4% 3-iodo-1-propanol as initiator. Stannous octoate is used as catalyst. The polymer is isolated, dissolved in dichloromethane, and precipitated into cold isopropanol to remove impurities, then dried before analysis and storage.

Degradable ureter stents are produced by first creating a coiled construct with MG5-B as described in Example 1, without the radiopaque additive. Glycoprene multifilament fiber is weft knitted over the coil component. RS-1 is dissolved in acetone and the coil/knit components are coated via continuous dip coating to create a coated scaffold. The coated scaffold is formed into the stent net shape as described in Example 6.

The coating prepared from RS-1, as a result of iodine content within the polymer, is inherently radiopaque, creating a stent that can be visualized by x-ray after implantation. As opposed to other disclosed stent structures described in earlier examples which contain solid inorganic particulate as a radiopacifier, the stent in this example contains no solid inorganic microparticulate. As the stent degrades in vivo, the absence of inorganic microparticulates minimizes the inflammatory response resulting from high hardness microparticulates.

Although any methods and materials similar or equivalent to those described herein can also be used in the practice or testing of the present invention, a limited number of the exemplary methods and materials are described herein. Generally, unless otherwise indicated, the materials for making the invention and/or its components may be selected from appropriate materials such as biodegradable polymers.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All publications and patents cited herein are incorporated herein by reference in their entirety for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

What is claimed is:

1. A medical implant comprising a containment layer that partially encases a ureteral stent, the ureteral stent comprising a degradable thermoplastic continuous coil with a hollow center and a continuous knitted scaffold located over the coil, the containment layer being in a form of a plurality of relatively wide circumferential bands that impregnate the ureteral stent, the relatively wide circumferential bands alternating with and therefore being separated from one another by a plurality of relatively narrow circumferential bands that do not comprise containment layer, the ureteral stent being at least partially biodegradable when the implant is implanted in a host, each circumferential band of the containment layer being either nonbiodegradable or biodegradable, where the relatively narrow circumferential bands provide defects that are present solely to impact a degradation profile of the medical implant, where the defects provide sites where degradation will preferentially occur vis-à-vis other sites of the medical implant as the medical implant degrades in vivo, and where the medical implant is a graduated implant such that a proximal end of the medical device or portion thereof degrades more rapidly than does a distal end of the medical implant due to a gradient in the properties of the narrow circumferential bands.

2. The implant of claim 1 wherein the containment layer is hydrophilic.

3. The implant of claim 1 wherein the containment layer is biodegradable, but the containment layer degrades more slowly than the ureteral stent.

4. The implant of claim 1 wherein the containment layer has a thickness of greater than 20 microns.

5. The implant of claim 1 wherein the containment layer has a thickness of greater than 40 microns.

6. The implant of claim 1 wherein the containment layer has a thickness of greater than 60 microns.

7. The implant of claim 1 wherein the containment layer has a thickness of greater than 80 microns.

8. The implant of claim 1 wherein the containment layer has a thickness of greater than 100 microns.

9. The implant of claim 1 wherein the containment layer has a thickness of greater than 120 microns.

10. A method of forming the medical implant of claim 1, the method comprising preparing the continuous coil with the hollow center, knitting the continuous knitted scaffold over the continuous coil to provide the ureteral stent, coating the ureteral stent with a polymer solution to provide the containment layer that impregnates the ureteral stent and comprises the polymer, removing a plurality of circumferential bands of the containment layer from the ureteral stent to provide a plurality of relatively wide circumferential bands that impregnate the ureteral stent, the relatively wide circumferential bands alternating with and therefore being separated from one another by the plurality of relatively narrow circumferential bands that do not comprise containment layer, so as to provide the medical implant.

* * * * *